(12) United States Patent
Kameshima et al.

(10) Patent No.: US 8,436,314 B2
(45) Date of Patent: May 7, 2013

(54) IMAGING APPARATUS, IMAGING SYSTEM, METHOD OF CONTROLLING THE APPARATUS AND THE SYSTEM, AND PROGRAM

(75) Inventors: Toshio Kameshima, Kumagaya (JP); Tadao Endo, Honjo (JP); Tomoyuki Yagi, Honjo (JP); Katsuro Takenaka, Honjo (JP); Keigo Yokoyama, Honjo (JP); Sho Sato, Kumagaya (JP); Toshikazu Tamura, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/393,396

(22) PCT Filed: Aug. 31, 2010

(86) PCT No.: PCT/JP2010/005346
§ 371 (c)(1),
(2), (4) Date: Feb. 29, 2012

(87) PCT Pub. No.: WO2011/027538
PCT Pub. Date: Mar. 10, 2011

(65) Prior Publication Data
US 2012/0199749 A1    Aug. 9, 2012

(30) Foreign Application Priority Data

Sep. 4, 2009 (JP) ................................ 2009-204719
Jul. 14, 2010 (JP) ................................ 2010-159885

(51) Int. Cl.
*H01L 27/146* (2006.01)
*H04N 3/14* (2006.01)

(52) U.S. Cl.
USPC ................. 250/370.08; 250/370.09; 348/296; 348/297; 348/298; 348/299; 348/300; 348/301; 348/302; 348/303; 348/304; 348/305; 348/306; 348/307; 348/308

(58) Field of Classification Search ............. 250/370.08, 250/370.09; 348/296–308
See application file for complete search history.

(56) References Cited

U.S. PATENT DOCUMENTS

2007/0237429 A1* 10/2007 Kusaka ......................... 382/312
2007/0297562 A1* 12/2007 Konno et al. .................... 378/12
2009/0154779 A1*  6/2009 Satyan et al. ................. 382/124

FOREIGN PATENT DOCUMENTS

| JP | 11128213 A | 5/1999 |
|----|------------|--------|
| JP | 11318877 A | 11/1999 |
| JP | 2001195563 A | 7/2001 |

(Continued)

*Primary Examiner* — David Porta
*Assistant Examiner* — Mindy Vu
(74) *Attorney, Agent, or Firm* — Canon U.S.A., Inc. IP Division

(57) ABSTRACT

An imaging apparatus includes a control unit and a detector that includes multiple pixels and that performs an image capturing operation to output image data corresponding to radiation or light that is emitted. The image capturing operation includes a first image capturing operation in a first scanning area corresponding to part of the multiple pixels to output image data in the first scanning area and a second image capturing operation in a second scanning area larger than the first scanning area to output image data in the second scanning area. The control unit causes the detector to perform an accumulation operation in the second image capturing operation in a time determined so that an image artifact caused by the scanning area is lower than a predetermined allowable value on the basis of information about the amount of integration of accumulation times in the first image capturing operation.

8 Claims, 19 Drawing Sheets

FOREIGN PATENT DOCUMENTS

| | | | |
|---|---|---|---|
| JP | 3275803 | B2 | 4/2002 |
| JP | 2006267093 | A | 10/2006 |
| JP | 3897389 | B2 | 3/2007 |
| JP | 2007173986 | A | 7/2007 |
| JP | 2007330302 | A | 12/2007 |
| JP | 2008167846 | A | 7/2008 |
| JP | 2008259045 | A | 10/2008 |

* cited by examiner

IMAGING APPARATUS, IMAGING SYSTEM, METHOD OF CONTROLLING THE APPARATUS AND THE SYSTEM, AND PROGRAM

TECHNICAL FIELD

The present invention relates to an imaging apparatus, a radiation imaging apparatus, an imaging system, a method of controlling the apparatuses and the system, and a program. Specifically, the present invention relates to an imaging apparatus used in a radiation imaging system, an imaging system, a method of controlling the apparatus and the system, and a program that are preferably used in capturing of still images, such as photography, and recording of movies, such as fluoroscopy, in medical diagnosis. In embodiments of the present invention, the radiation include not only alpha rays, beta rays, and gamma rays, which are beams made of particles (including photons) emitted due to radiation damage, but also beams, such as X rays, particle beams, and cosmic rays, having the energies of at least the same level as those of the alpha rays, the beta rays, and the gamma rays.

BACKGROUND ART

In recent years, radiation imaging apparatuses using flat panel detectors (hereinafter abbreviated as FPDs) made of semiconductor materials have come into practical use as image capturing apparatuses used in medical image diagnosis and non-destructive tests using X rays. Such radiation imaging apparatuses are used as digital imaging apparatuses for capturing of still image, such as photography, and recording of movies, such as fluoroscopy, for example, in the medial image diagnosis.

Arbitrary switching of the areas (field-of-view sizes) where the readout by the FPDs is performed is discussed in such a radiation imaging apparatus, as disclosed in Patent Documents 1 and 2.

CITATION LIST

Patent Literature

PTL 1: Japanese Patent Laid-Open No. 11-128213
PTL 2: Japanese Patent Laid-Open No. 11-318877

SUMMARY OF INVENTION

Technical Problem

However, when the areas are expanded as the result of the switching, the areas where the scanning by the FPD is performed differ from the areas where the scanning by the FPD is not performed in the sensitivity of pixels and/or the dark time outputs. Accordingly, ghost (difference in level) affected by the readout area (scanning area) can occur in an image that is captured to cause a reduction in image quality.

Solution to Problem

The present invention provides an imaging apparatus and an imaging system capable of reducing the difference in level that can occur in a captured image and that is affected by the scanning area to prevent a significant reduction in image quality.

According to an embodiment of the present invention, an imaging system includes an imaging apparatus including a detector in which a plurality of pixels each including a conversion element that converts radiation or light into an electric charge are arranged in a matrix form and which performs an image capturing operation to output image data corresponding to radiation or light that is emitted and a control unit that controls operations including the image capturing operation of the detector; and a control computer configured to control the imaging apparatus. The image capturing operation includes a first image capturing operation and a second image capturing operation. The first image capturing operation includes a first accumulation operation in which the conversion element generates the electric charge and a first output operation in which the detector is scanned in a first scanning area corresponding to part of the plurality of pixels to output image data in the first scanning area. The second image capturing operation includes a second accumulation operation in which the conversion element generates the electric charge and a second output operation in which the detector is scanned in a second scanning area larger than the first scanning area to output image data in the second scanning area. If switching from the first scanning area to the second scanning area is performed, the control computer performs arithmetic processing so that an image artifact caused by the scanning area is lower than a predetermined allowable value on the basis of information about the amount of integration of accumulation times in the first image capturing operation and supplies a control signal based on the time of the second accumulation operation determined in the arithmetic processing to the control unit. The control unit controls the operation of the detector so that the second accumulation operation is performed in the time of the second accumulation operation determined in the arithmetic processing.

According to another embodiment of the present invention, an imaging apparatus includes a detector in which a plurality of pixels each including a conversion element that converts radiation or light into an electric charge are arranged in a matrix form and which performs an image capturing operation to output image data corresponding to radiation or light that is emitted; and a control unit configured to control operations including the image capturing operation of the detector. The image capturing operation includes a first image capturing operation and a second image capturing operation. The first image capturing operation includes a first accumulation operation in which the conversion element generates the electric charge and a first output operation in which the detector is scanned in a first scanning area corresponding to part of the plurality of pixels to output image data in the first scanning area. The second image capturing operation includes a second accumulation operation in which the conversion element generates the electric charge and a second output operation in which the detector is scanned in a second scanning area larger than the first scanning area to output image data in the second scanning area. If switching from the first scanning area to the second scanning area is performed, the control unit causes the detector to perform the second accumulation operation in a time determined by arithmetic processing so that an image artifact caused by the scanning area is lower than a predetermined allowable value on the basis of information about the amount of integration of accumulation times in the first image capturing operation.

According to another embodiment of the present invention, a method of controlling an imaging apparatus that includes a detector in which a plurality of pixels each including a conversion element that converts radiation or light into an electric charge are arranged in a matrix form and which performs an image capturing operation to output image data corresponding to radiation or light that is emitted and that controls operations including the image capturing operation of the detector. The method includes the step of performing a second image capturing operation after a first image capturing operation. The first image capturing operation includes a first accumulation operation in which the conversion element generates the electric charge and a first output operation in which the detector is scanned in a first scanning area corresponding to part of the plurality of pixels to output image data in the first scanning area. The second image capturing operation includes a second accumulation operation in which the conversion element generates the electric charge and which is performed in a time determined in arithmetic processing so that an image artifact caused by the scanning area is lower than a predetermined allowable value on the basis of information about the amount of integration of accumulation times in the first image capturing operation and a second output operation in which the detector is scanned in a second scanning area larger than the first scanning area to output image data in the second scanning area.

According to another embodiment of the present invention, a program causes a computer to control an imaging apparatus that includes a detector in which a plurality of pixels each including a conversion element that converts radiation or light into an electric charge are arranged in a matrix form and which performs an image capturing operation to output image data corresponding to radiation or light that is emitted and that controls operations including the image capturing operation of the detector. The program causes the computer to perform a second image capturing operation after a first image capturing operation. The first image capturing operation includes a first accumulation operation in which the conversion element generates the electric charge and a first output operation in which the detector is scanned in a first scanning area corresponding to part of the plurality of pixels to output image data in the first scanning area. The second image capturing operation includes a second accumulation operation in which the conversion element generates the electric charge and which is performed in a time determined in arithmetic processing so that an image artifact caused by the scanning area is lower than a predetermined allowable value on the basis of information about the amount of integration of accumulation times in the first image capturing operation and a second output operation in which the detector is scanned in a second scanning area larger than the first scanning area to output image data in the second scanning area.

Advantageous Effects of Invention

According to the present invention, the drive operation of the FPD unit allows ghost (difference in level) that can occur in an acquired image and that is affected by the scanning area to be reduced to prevent a considerable reduction in image quality.

DESCRIPTION OF EMBODIMENTS

Embodiments of the present invention will herein be described in detail with reference to the attached drawings.

First Embodiment

Figure 1:
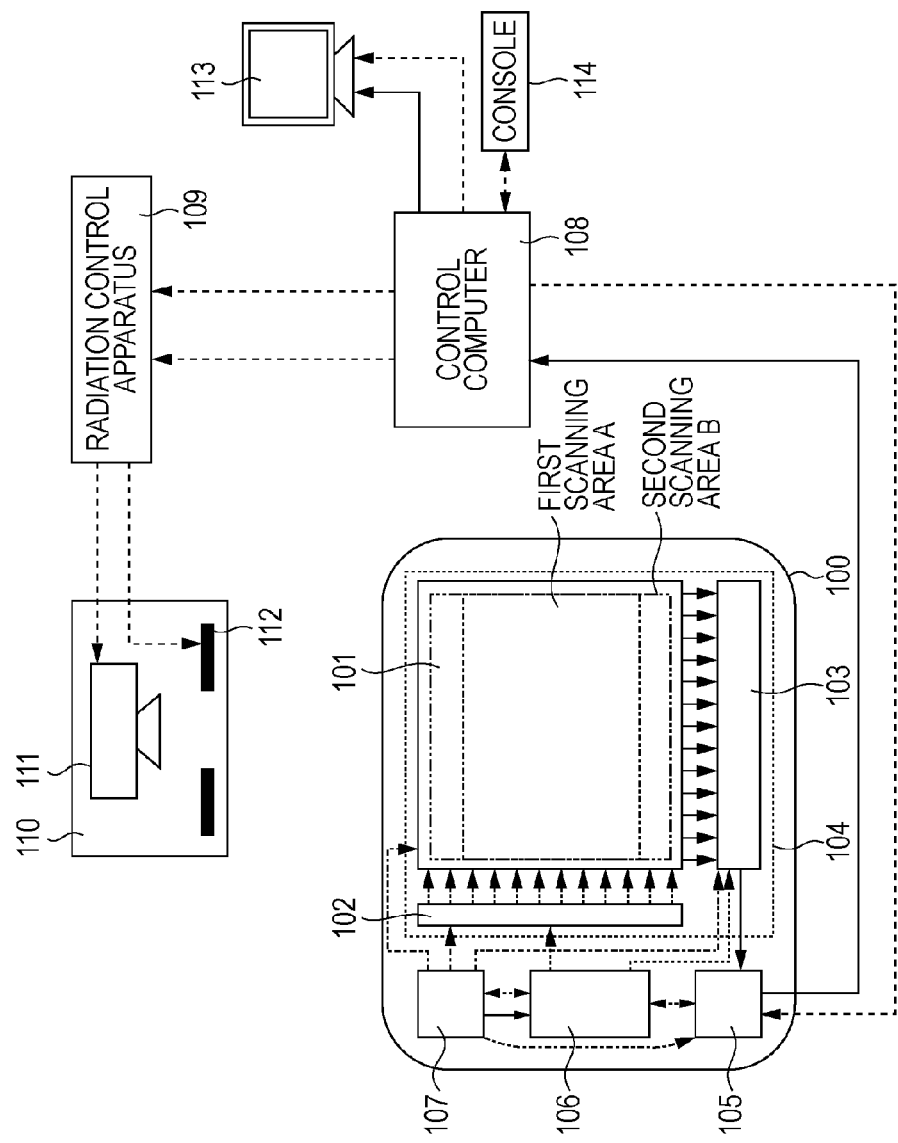
FIG. 1 is a conceptual block diagram illustrating an imaging system including an imaging apparatus according to a first embodiment of the present invention.

FIG. 1 is a conceptual block diagram illustrating a radiation imaging system including an imaging apparatus according to a first embodiment of the present invention. Referring to FIG. 1, the radiation imaging system includes an imaging apparatus 100, a control computer 108, a radiation control apparatus 109, a radiation generating apparatus 110, a display apparatus 113, and a console 114. The imaging apparatus 100 includes an FPD 104 including a detection unit 101, a drive circuit 102, and a readout circuit 103. The detection unit 101 includes multiple pixels each converting radiation or light into an electrical signal. The drive circuit 102 drives the detection unit 101. The readout circuit 103 outputs the electrical signal supplied from the detection unit 101 that is driven as image data. The imaging apparatus 100 further includes a signal processing unit 105 that processes the image data supplied from the FPD 104 to output the image data subjected to the processing, a control unit 106 that supplies a control signal to each component to control the operation of the FPD 104, and a power supply unit 107 that supplies a bias voltage to each component. The signal processing unit 105 receives a control signal from the control computer 108 described below to supply the received control signal to the control unit 106. The control unit 106 controls the drive circuit 102 so that switching between at least two scanning areas is performed in response to a control signal received from the control computer 108 described below. The drive circuit 102 is configured to be capable of switching between the scanning areas in response to the control signal received from the control unit 106. According to the first embodiment, the control unit 106 has a function of switching between a first scanning area A and a second scanning area B. In the first scanning area A in the first embodiment, part of the multiple pixels is scanned by the drive circuit 102. For example, when the sum of the number of pixels is equal to about 2,800 lines by about 2,800 columns, pixels of about 1,000 lines by about 2,800 columns are scanned by the drive circuit 102. In the second scanning area B in the first embodiment, pixels within a range larger than that of the first scanning area A, for example, all the pixels are scanned. The power supply unit 107 includes a power supply circuit, such as a regulator, which receives a voltage from an external power supply or a built-in battery (not shown) to supply a voltage necessary in the detection unit 101, the drive circuit 102, and the readout circuit 103.

The control computer 108 performs synchronization between the radiation generating apparatus 110 and the imaging apparatus 100, transmission of the control signals for determining the state of the imaging apparatus 100, and image processing for correcting, storing, and/or displaying the image data from the imaging apparatus 100. In addition, the control computer 108 transmits a control signal for determining irradiation conditions of the radiation on the basis of information from the console 114 to the radiation control apparatus 109.

The radiation control apparatus 109 controls an operation to emit radiation from a radiation source 111 included in the radiation generating apparatus 110 and the operation of a radiation field limiting mechanism 112 in the radiation generating apparatus 110 in response to the control signal received from the control computer 108. The radiation field limiting mechanism 112 has a function of changing a certain radiation field which is irradiated with the radiation or the light corresponding to the radiation and which is in the detection unit 101 in the FPD 104. The console 114 is used by an operator to input information about a subject and image capturing conditions, which are used as parameters in a variety of control in the control computer 108, and transmits the information and the image capturing conditions to the control computer 108. The display apparatus 113 displays the image data subjected to the image processing in the control computer 108.

Figure 2:
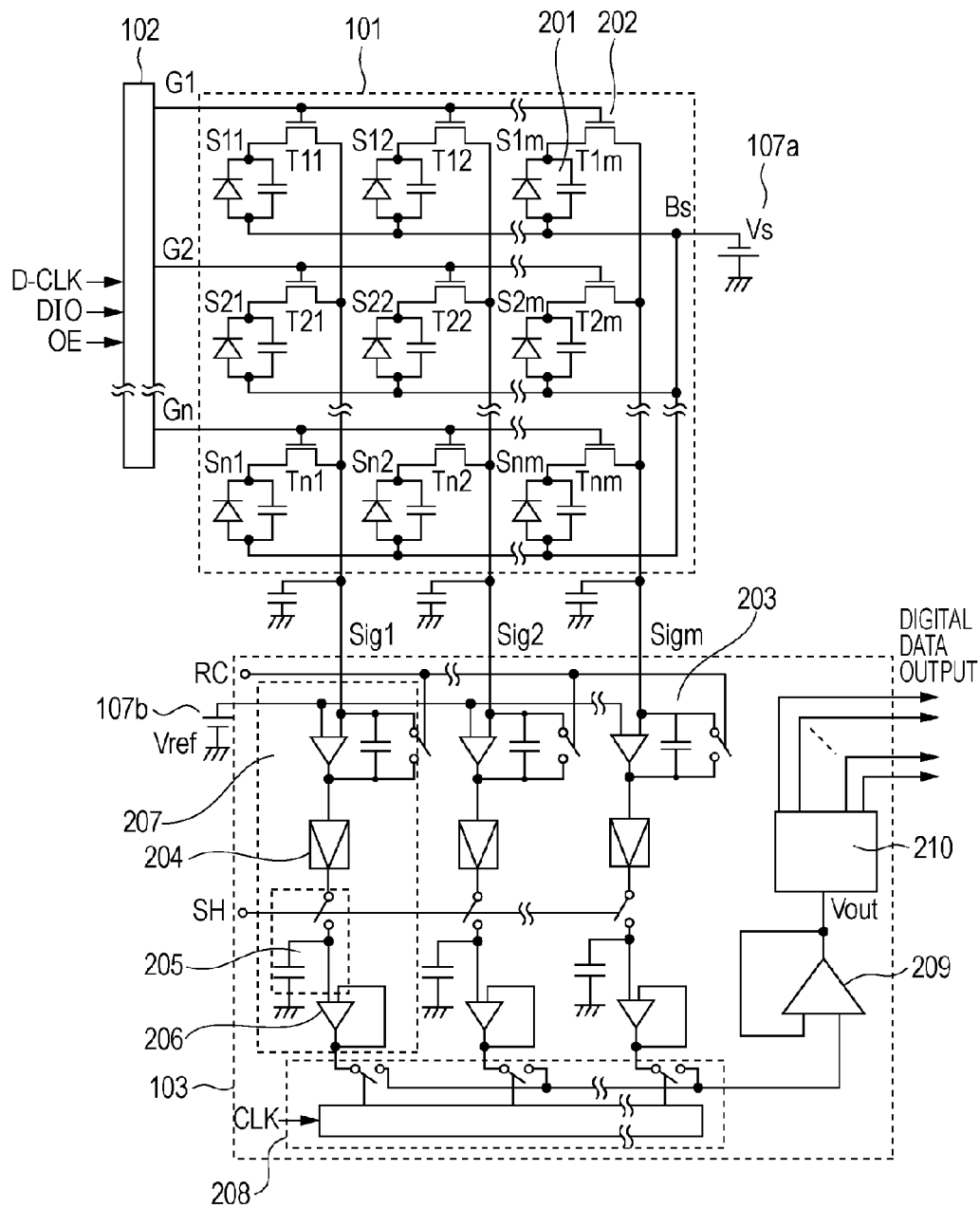
FIG. 2 is a conceptual equivalent circuit of the imaging apparatus according to the first embodiment of the present invention.

FIG. 2 is a conceptual equivalent circuit of the imaging apparatus according to the first embodiment of the present invention. The same reference numerals are used in FIG. 2 to identify the same components shown in FIG. 1. A detailed description of such components is omitted herein. The imaging apparatus in FIG. 2 includes the FPD unit including pixels of n lines by m columns for convenience, where each of n and m is an integer that is equal to or larger than two. The imaging apparatus practically includes the pixels of a number that is larger than n lines by m columns. For example, a 17-inch imaging apparatus includes pixels of about 2,800 lines by about 2,800 columns.

The detection unit 101 includes multiple pixels that are arranged in a matrix form. Each pixel has a conversion element 201 that converts the radiation or the light into an electric charge and a switch element 202 that outputs an electrical signal corresponding to the electric charge. In the first embodiment, a PIN photodiode that is arranged on an insulating substrate, such as a glass substrate, and that is mainly made of an amorphous silicon material is used as the photoelectric transducer converting the light with which the conversion element is irradiated into the electric charge. An indirect conversion element provided with a wavelength converter at the incident side of the radiation of the above photoelectric transducer or a direct conversion element directly converting the radiation into the electric charge is preferably used as the conversion element 201. The wavelength converter converts radiation into light within a waveband that can be detected by the photoelectric transducer. A transistor having a control terminal and two main terminals is preferably used as the switch element 202. A thin film transistor (TFT) is used as the switch element 202 in the first embodiment. One electrode of the conversion element 201 is electrically connected to one of the two main terminals of the switch element 202 and the other electrode of the conversion element 201 is electrically connected to a bias power supply 107a via a common bias line Bs. The control terminals of the multiple switch elements in the line direction, for example, the switch elements T11 to T1m are commonly electrically connected to a first-line drive line G1. A drive signal for controlling the conductive state of the switch element is supplied from the drive circuit 102 to each switch element in each line via the drive line. The drive circuit 102 controls the conductive state and the non-conductive state of the switch elements 202 for every line to scan the pixels for every line. The scanning area in the embodiments of the present invention means an area where the drive circuit 102 scans the pixels for every line, as described above. Although the pixels of n lines by m columns are shown in FIG. 2 for convenience, the pixels of about 1,000 lines by about 2,800 columns are practically scanned by the drive circuit 102 as the first scanning area A when the sum of the number of pixels is equal to, for example, about 2,800 lines by about 2,800 columns The remaining main terminal of each of the multiple switch elements in the column direction, for example, the switch elements T11 to Tn1 is electrically connected to a first-column signal line Sig1. The electrical signal corresponding to the electric charge of the conversion element is supplied to the readout circuit 103 through the signal line while the switch element is in the conductive state. The electrical signals output from the multiple pixels are transmitted to the readout circuit 103 in parallel through the multiple signal lines Sig1 to Sigm arranged in the column direction.

The readout circuit 103 includes an amplifier circuit 207 for every signal line. The amplifier circuit 207 amplifies each of the electrical signals output in parallel from the detection unit 101. The amplifier circuit 207 includes an integrating amplifier 203 that amplifies the output electrical signal, a variable amplifier 204 that amplifies the electrical signal from the integrating amplifier 203, a sample-and-hold circuit 205 that samples and holds the amplified electrical signal, and a buffer amplifier 206. The integrating amplifier 203 includes an operational amplifier that amplifies the readout electrical signal and outputs the amplified electrical signal, an integration capacitor, and a reset switch. The integrating amplifier 203 is capable of varying the value of the integration capacitor to change the gain. The output electrical signal is input into an inverting input terminal of the operational amplifier, a reference voltage Vref is supplied from a reference power supply 107b to a non-inverting input terminal of the operational amplifier, and the amplified electrical signal is output from an output terminal of the operational amplifier. The integration capacitor is arranged between the inverting input terminal and the output terminal of the operational amplifier. The sample-and-hold circuit 205 is provided for every amplifier circuit and includes a sampling switch and a sampling capacitor. The readout circuit 103 includes a multiplexer 208 that sequentially outputs the electrical signals read out in parallel from the amplifier circuit 207 as a serial image signal and a buffer amplifier 209 that performs impedance conversion to the image signal to output the image signal subjected to the impedance conversion. An image signal Vout, which is an analog electrical signal output from the buffer amplifier 209, is converted into digital image data in an analog-to-digital (A/D) converter 210 and the digital image data is supplied to the signal processing unit 105. The image data processed in the signal processing unit 105 in FIG. 1 is transmitted to the control computer 108.

The drive circuit 102 supplies a drive signal including a conductive voltage Vcom setting the switch element to the conductive state and a non-conductive voltage Vss setting the switch element to the non-conductive state to each drive line in response to the control signal (D-CLK, OE, or DIO) supplied from the control unit 106 in FIG. 1. The drive circuit 102 controls the conductive state and the non-conductive state of the switch element with the control signal to drive the detection unit 101.

The power supply unit 107 in FIG. 1 includes the bias power supply 107a and the reference power supply 107b for the amplifier circuit 207 shown in FIG. 2. The bias power supply 107a supplies a bias voltage Vs to the other electrode of each conversion element through the bias line Bs. The reference power supply 107b supplies the reference voltage Vref to the non-inverting input terminal of each operational amplifier.

The control unit 106 in FIG. 1 receives the control signals from the control computer 108, etc. outside the imaging apparatus via the signal processing unit 105 and supplies the control signals to the drive circuit 102, the power supply unit 107, and the readout circuit 103 to control the operation of the FPD 104. The control unit 106 supplies the control signal D-CLK, the control signal OE, and the control signal DIO to the drive circuit 102 to control the operation of the drive circuit 102. The control signal D-CLK is a shift clock for a shift register used as the drive circuit, the control signal DIO is a pulse signal transferred by the shift register, and the control signal OE is used to control the output end of the shift register. The control unit 106 is capable of controlling the drive circuit 102 with these control signals to switch between the first scanning area A and the second scanning area B. In addition, the control unit 106 supplies a control signal RC, a control signal SH, and a control signal CLK to the readout circuit 103 to control the operation of each component in the readout circuit 103. The control signal RC is used to control the operation of the reset switch in the integrating amplifier 203, the control signal SH is used to control the operation of the sample-and-hold circuit 205, and the control signal CLK is used to control the operation of the multiplexer 208.

Figure 3:
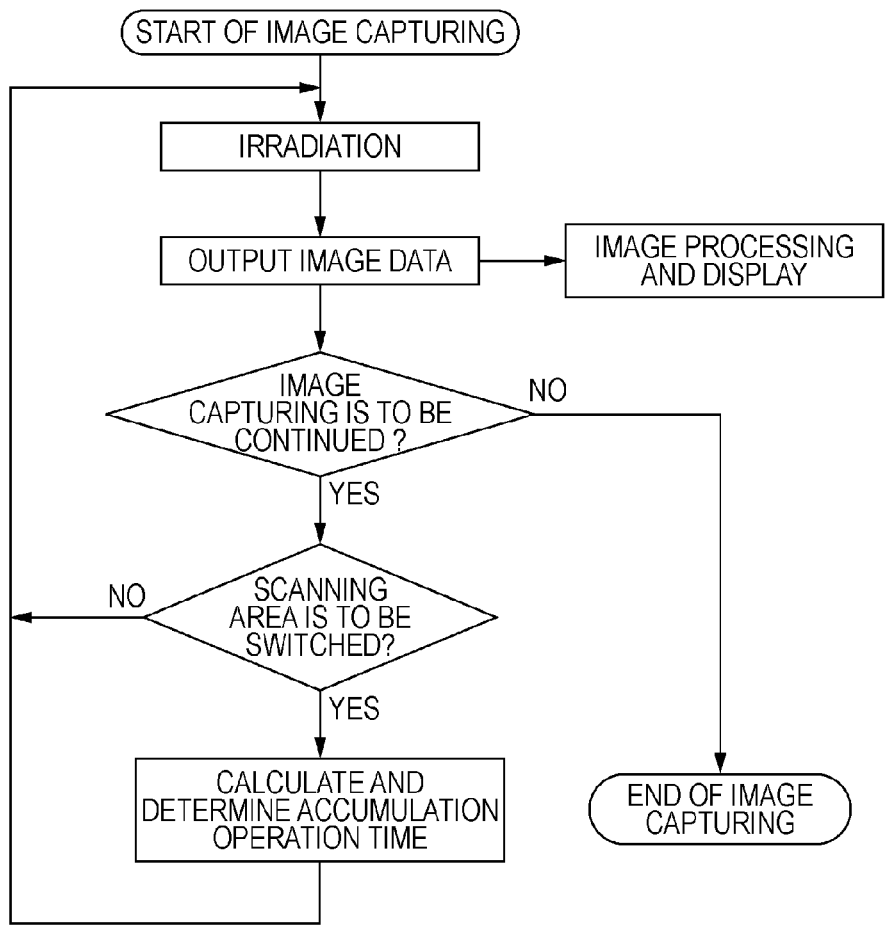
FIG. 3 is a flowchart showing an example of the operation of the imaging apparatus and the imaging system according to embodiments of the present invention.

An example of the operation of the imaging apparatus and the entire imaging system according to an embodiment of the present invention will now be described with reference to FIGS. 1 to 3, especially with reference to FIG. 3. After the irradiation conditions are determined by the control computer 108 in response to an operation of the operator with the console 114, the image capturing is started. An object is irradiated with desired radiation emitted from the radiation generating apparatus 110 controlled by the radiation control apparatus 109 under the determined irradiation conditions. The imaging apparatus 100 outputs image data corresponding to the radiation transmitted through the object. The output image data is subjected to the image processing in the control computer 108 and is displayed in the display apparatus 113.

The control computer 108 asks the operator whether the image capturing is to be continued. If an instruction not to continue the image capturing is received from the operator (NO), the image capturing is terminated. If an instruction to continue the image capturing is received from the operator (YES), the control computer 108 asks the operator whether the scanning area is to be switched to. If an instruction not to switch the scanning area is received from the operator (NO), the control computer 108 controls the radiation control apparatus 109 and the radiation generating apparatus 110 under the image capturing conditions that have been determined to irradiate the object with the radiation again under the same conditions. If an instruction to switch the scanning area is received from the operator (YES), the control computer 108 determines the scanning area to be switched to. Then, the control computer 108 performs arithmetic processing to determine an accumulation operation time described below. Then, the control computer 108 supplies the control signal based on the scanning area and the accumulation operation time that are determined to the imaging apparatus 100 to perform the next image capturing in the determined scanning area in the determined accumulation operation time.

Figure 4A:
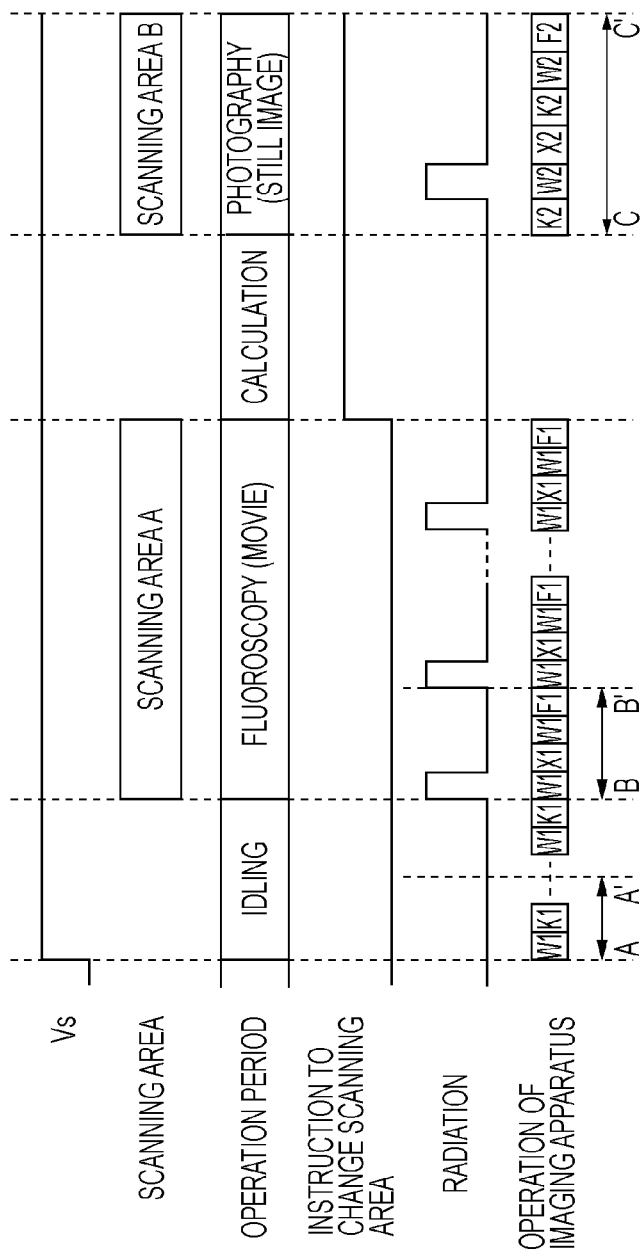
FIG. 4A is a timing chart illustrating the entire operation of the imaging apparatus and the imaging system according to the first embodiment of the present invention.

Examples of the operations of the imaging system according to the first embodiment of the present invention will now be described with reference to FIGS. 4A to 4D. Referring to FIG. 4A, upon supply of the bias voltage Vs to the conversion element 201, the imaging apparatus 100 performs idling during an idling period. In the idling operation, at least an initialization operation K1 is repeated multiple times in order to stabilize the variation in characteristics of the FPD 104, caused by the start of the supply of the bias voltage Vs. The initialization operation is an operation to apply an initial bias voltage before the accumulation operation to the conversion element to initialize the conversion element. In the example in FIG. 4A, a pair of an accumulation operation W1 and the initialization operation K1 is repeated multiple times as the idling operation.

Figure 4B:
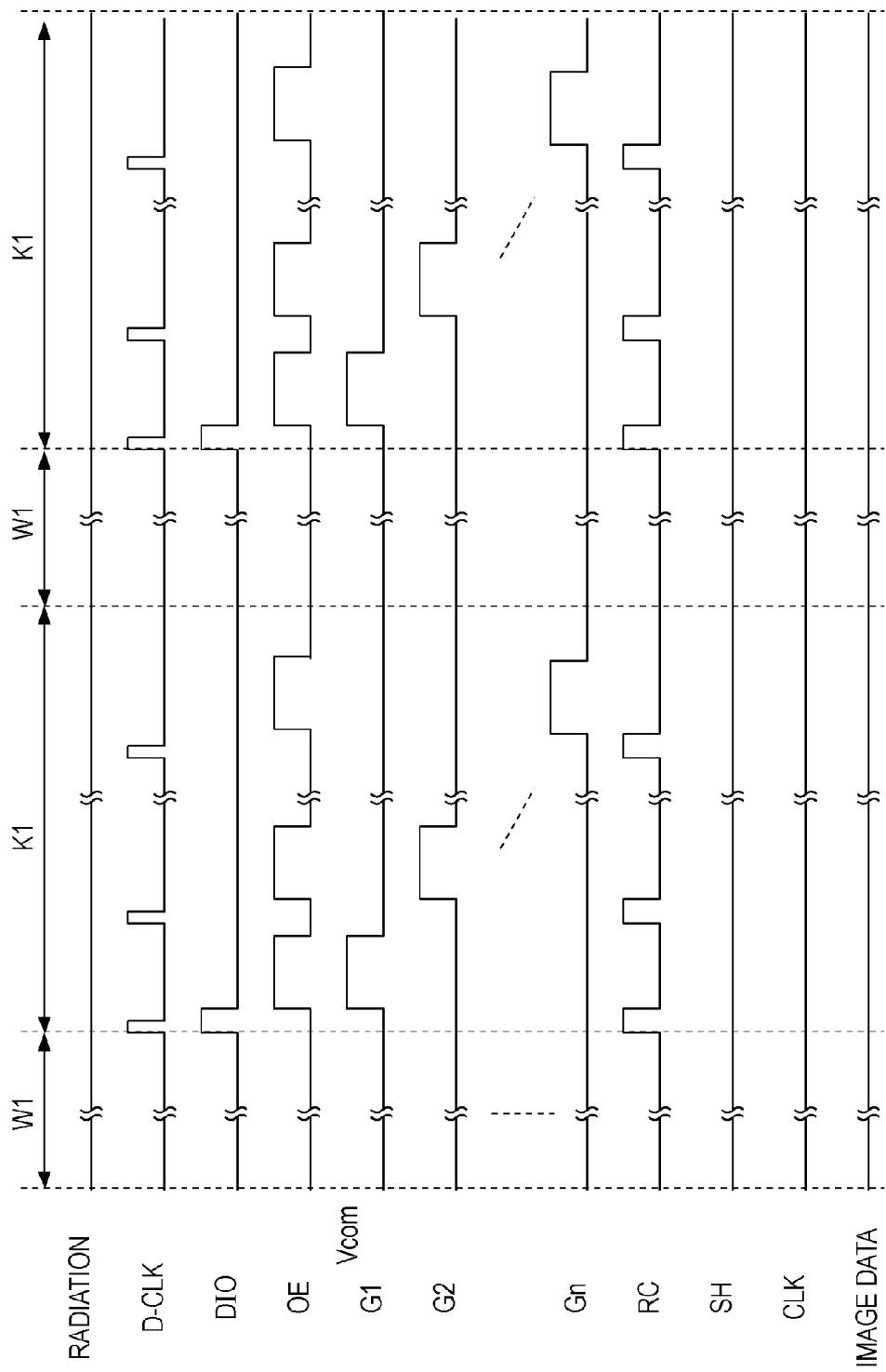
FIG. 4B is a timing chart illustrating an operation of the imaging apparatus and the imaging system according to the first embodiment of the present invention.

FIG. 4B is a timing chart illustrating an example of the operation of the imaging apparatus during a period A-A' in FIG. 4A. Referring to FIG. 4B, in the accumulation operation W1, the non-conductive voltage Vss is applied to the switch element 202 with the bias voltage Vs applied to the conversion element 201 to set the switch elements in all the pixels to the non-conductive state. In the initialization operation K1, the integration capacitor in the integrating amplifier 203 and the signal line are reset by the reset switch and the conductive voltage Vcom is applied from the drive circuit 102 to the drive line G1 to set the switch elements T11 to T1$m$ in the first line to the conductive state. Setting the switch elements to the conductive state causes the conversion elements to be initialized. Although the electric charge of each conversion element is output from the corresponding switch element as the electrical signal in this state, no data corresponding to the electrical signal is output from the readout circuit 103 because the sample-and-hold circuit and the subsequent circuits are not operated in the first embodiment. The integration capacitor and the signal line are reset again later to process the output electrical signal. However, when the data is to be used for correction, etc., the sample-and-hold circuit and the subsequent circuits may be operated in a manner similar to that of an image output operation or a dark image output operation described below. Repeating the control of the conductive state of the switch element and the resetting from the first line to the n-th line causes the detection unit 101 to be initialized. In the initialization operation, the reset switch may be kept in the conductive state to continue the resetting at least while the switch element is in the conductive state. The time when the switch element is in the conductive state in the initialization operation may be shorter than the time when the switch element is in the conductive state in the image output operation described below. In addition, the switch elements in multiple lines may be simultaneously conducted in the initialization operation. In such cases, it is possible to reduce the time required for the entire initialization operation to rapidly stabilize the variation in characteristics of the FPD 104. The initialization operation K1 in the first embodiment is performed in the same period as that of the image output operation included in the fluoroscopy operation following the idling operation.

Figure 4C:
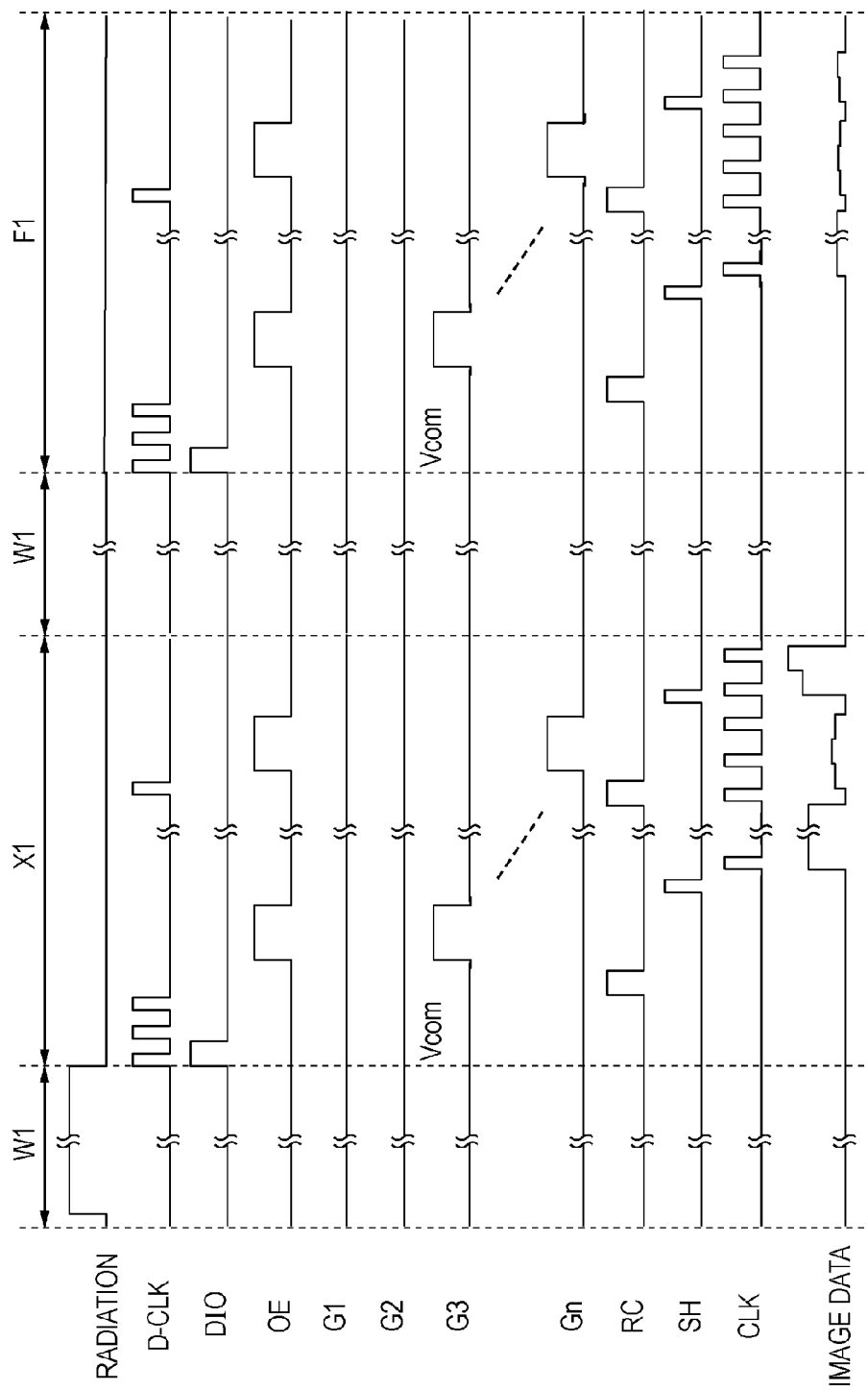
FIG. 4C is a timing chart illustrating another operation of the imaging apparatus and the imaging system according to the first embodiment of the present invention.

FIG. 4C is a timing chart illustrating an example of the operation of the imaging apparatus during a period B-B' in FIG. 4A. After the idling operation is performed to set the detection unit 101 to a state in which the image capturing can be performed, the imaging apparatus 100 performs the fluoroscopy operation in which the FPD 104 is scanned in the first scanning area A in response to the control signal from the control computer 108. The fluoroscopy operation corresponds to a first image capturing operation. In the first image capturing operation, image data corresponding to the first scanning area is output from the FPD 104 scanned in the first scanning area. The period during which the imaging apparatus 100 performs the fluoroscopy operation is called a fluoroscopy period. During the fluoroscopy period, the imaging apparatus 100 performs the accumulation operation W1 performed during a period corresponding to the time period when the radiation is emitted in order to cause the conversion element 201 to generate the electric charge in response to the emitted radiation and an image output operation X1 in which image data is output on the basis of the electric charge generated in the accumulation operation W1. As shown in FIG. 4C, in the image output operation X1, the control unit 106 supplies the control signal D-CLK corresponding to the number of lines corresponding to the second scanning area to the drive circuit 102 with the control signal OE and the control signal DIO in a Lo state. Accordingly, the conductive voltage Vcom is not supplied from the drive circuit 102 to the drive lines G1 and G2 and, thus, the first and second lines corresponding to the second scanning area are not scanned. Then, the integration capacitor and the signal line are reset and the conductive voltage Vcom is applied from the drive circuit 102 to the drive line G3 to set the switch elements T31 to T3$m$ in the third line to the conductive state. As a result, the electrical signal based on the electric charge generated in conversion elements S31 to S3$m$ in the third line is supplied to each signal line. Each of the electrical signals output in parallel through the respective signal lines is amplified in the integrating amplifier 203 and the variable amplifier 204 in each amplifier circuit 207. The amplified electrical signals are held in parallel in the sample-and-hold circuits 205 in the respective amplifier circuits 207. The sample-and-hold circuits 205 are operated in response to the control signal SH. After the electrical signals are held, the integration capacitors and the signal lines are reset. After the resetting, the conductive voltage Vcom is applied to the drive line G4 in the fourth line, as in the third line, to set the switch elements T41 to T4$m$ in the fourth line to the conductive state. During the period in which the switch elements T41 to T4$m$ in the fourth line are set to the conductive state, the multiplexer 208 sequentially outputs the electrical signals held in the sample-and-hold circuits 205. As a result, the electrical signals read out from the pixels in the first line in parallel are converted into a serial image signal and the serial image signal is output. The A/D converter 210 converts the image signal into image data corresponding to one line and outputs the image data resulting from the conversion. Performing the above operation for every line from the third line to the n-th lines causes the image data corresponding to one frame to be output from the imaging apparatus 100. In addition, in the first embodiment, the imaging apparatus 100 performs the accumulation operation W1 that is performed in the same period as that of the accumulation operation W1 described above in order to cause the conversion element 201 to generate the electric charge in a dark state in which the emission of the radiation is not performed and a dark image output operation F1 in which dark image data is output on the basis of the electric charge generated in the accumulation operation W1. In the dark image output operation F1, an operation similar to the image output operation X1 is performed in the imaging apparatus 100. The time resulting from addition of the time when the accumulation operation is performed to the time resulting from subtraction of the time when each switch element is in the conductive state from the time when the image output operation is performed is called an accumulation time. The time when each switch element is in the conductive state is called a scanning time. The time when one set of image capturing operations including the accumulation operation, the image output operation, the accumulation operation, and the dark image output operation is performed is called a frame time and a reciprocal of the frame time is called a frame speed. The accumulation operation W1 in the first embodiment corresponds to a first accumulation operation and the image output operation X1 or the dark image output operation F1 in the first embodiment corresponds to a first output operation. Although the pixels in the first and second lines are not scanned in the first embodiment, the present invention is not limited to this scanning mode. For example, all the second pixels corresponding to the pixels in the first and second lines may be simultaneously scanned or the second pixels may be scanned in a scanning period that is shorter than that of the first pixels in the first scanning area. In other words, the scanning may be performed so that the normal image capturing operation is not performed to the second pixels during the first image capturing operation. Although the pixels in the second scanning area are sequentially scanned in the initialization operation K1 in FIG. 4B, the present invention is not limited this scanning mode and the scanning may be performed in a manner similar to that of the image output operation X1.

Upon reception of the instruction to switch the scanning area from the console 114, the control computer 108 performs the arithmetic processing to determine the accumulation time in response to the instruction. The period in which the arithmetic processing is performed is called an arithmetic period. The arithmetic processing will be described in detail with reference to FIGS. 5A to 5C.

Figure 4D:
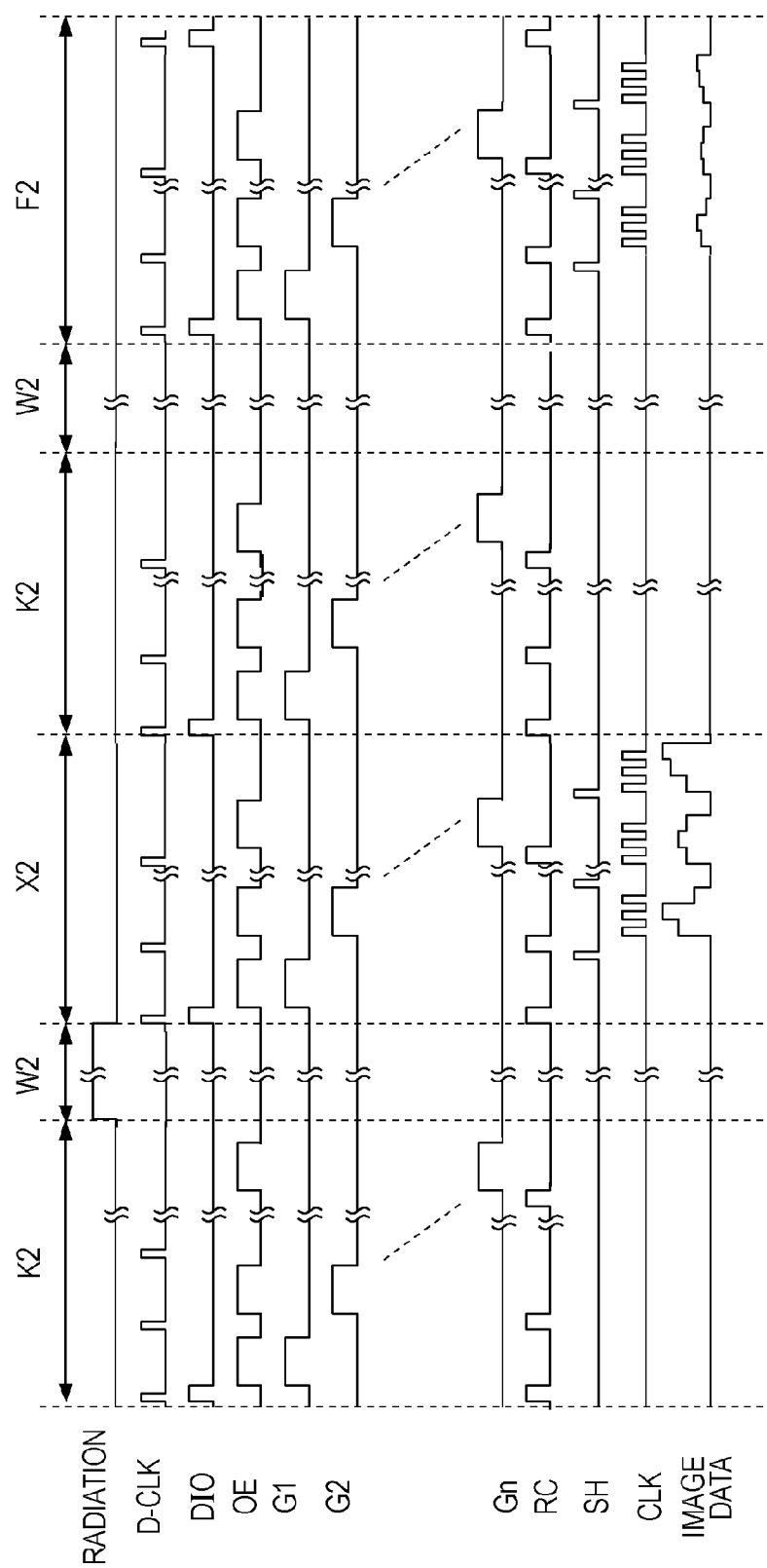
FIG. 4D is a timing chart illustrating another operation of the imaging apparatus and the imaging system according to the first embodiment of the present invention.

FIG. 4D is a timing chart illustrating an example of the operation of the imaging apparatus during a period C-C" in FIG. 4A. After the arithmetic processing, the control computer 108 supplies the control signal corresponding to the accumulation time determined in the arithmetic processing to the imaging apparatus 100. The imaging apparatus 100 performs the photography operation (capturing of still images) in which the FPD 104 is scanned in the second scanning area B larger than the first scanning area A in response to the control signal supplied from the control computer 108. The photography operation corresponds to a second image capturing operation. In the second image capturing operation, the image data corresponding to the second scanning area is output from the FPD 104 scanned in the second scanning area. The period in which the imaging apparatus 100 performs the photography operation is called a photography period. During the photography period, the imaging apparatus 100 performs an accumulation operation W2 performed in an accumulation operation time Tw, determined in the arithmetic processing, in order to cause the conversion element to generate the electric charge in response to the emitted radiation and an image output operation X2 in which image data is output on the basis of the electric charge generated in the accumulation operation W2. As shown in FIG. 4D, although the accumulation operation W2 in the first embodiment is similar to the accumulation operation W1, the accumulation operation W2 is differentiated from the accumulation operation W1 because the period of the accumulation operation W2 is different from that of the accumulation operation W1. In contrast, although the image output operation X2 is similar to the image output operation X1 except that the first and second lines are scanned in the same manner as in the third line and the subsequent lines, the image output operation X2 is differentiated from the image output operation X1 because the period of the image output operation X2 is longer than that of the image output operation X1. However, the accumulation operation W2 may be performed in the same period as that of the accumulation operation W1 and the image output operation X2 may be performed in the same period as that of the image output operation X1 depending on the result of the arithmetic processing. In addition, in the first embodiment, the imaging apparatus 100 performs the accumulation operation W2 performed in the same period as that of the accumulation operation W2 described above in order to cause the conversion element to generate the electric charge in the dark state in which the radiation is not emitted and a dark image output operation F2 in which dark image data is output on the basis of the electric charge generated in the accumulation operation W2. In the dark image output operation F2, an operation similar to the image output operation X2 is performed in the imaging apparatus 100. In addition, in the first embodiment, the imaging apparatus 100 performs an initialization operation K2 before each accumulation operation W2. Although the initialization operation K2 is similar to the initialization operation K1 described above, the initialization operation K2 is differentiated from the initialization operation K1 because the period of the initialization operation K2 is different from that of the initialization operation K1. However, as in the accumulation operation W2, the initialization operation K2 may be performed in the same period as that of the initialization operation K1 depending on the result of the arithmetic processing. The accumulation operation W2 in the first embodiment corresponds to a second accumulation operation and the image output operation X2 or the dark image output operation F2 in the first embodiment corresponds to a second output operation.

Figure 5A:
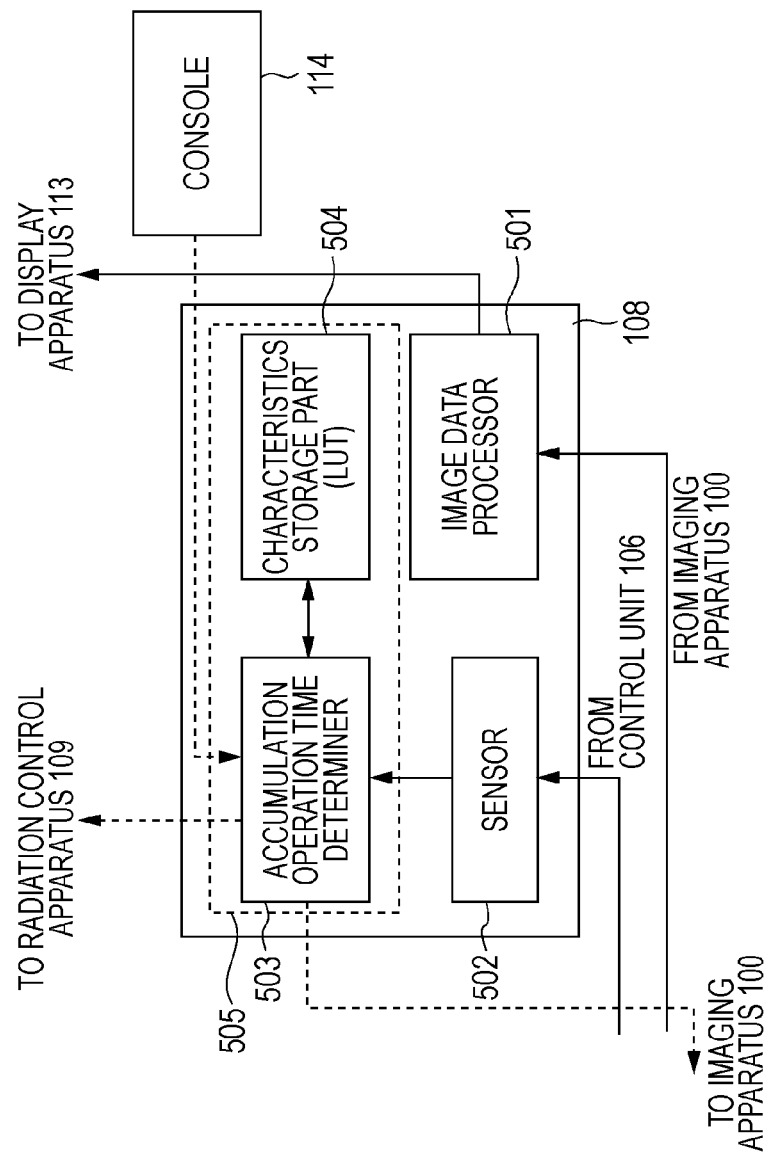
FIG. 5A schematically illustrates an example of the configuration of a control computer according to an embodiment of the present invention.
Figure 5B:
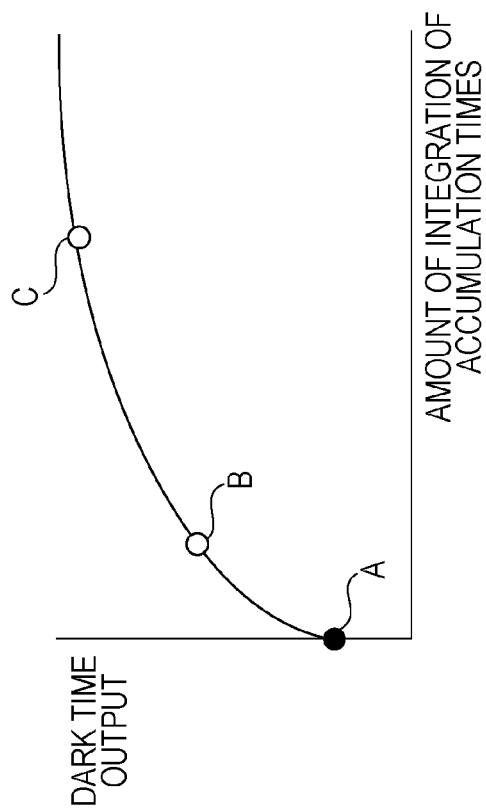
FIG. 5B is a characteristic diagram of the amount of integration of accumulation times and a dark time output illustrating the concept and advantages according to the embodiments of the present invention.
Figure 5C:
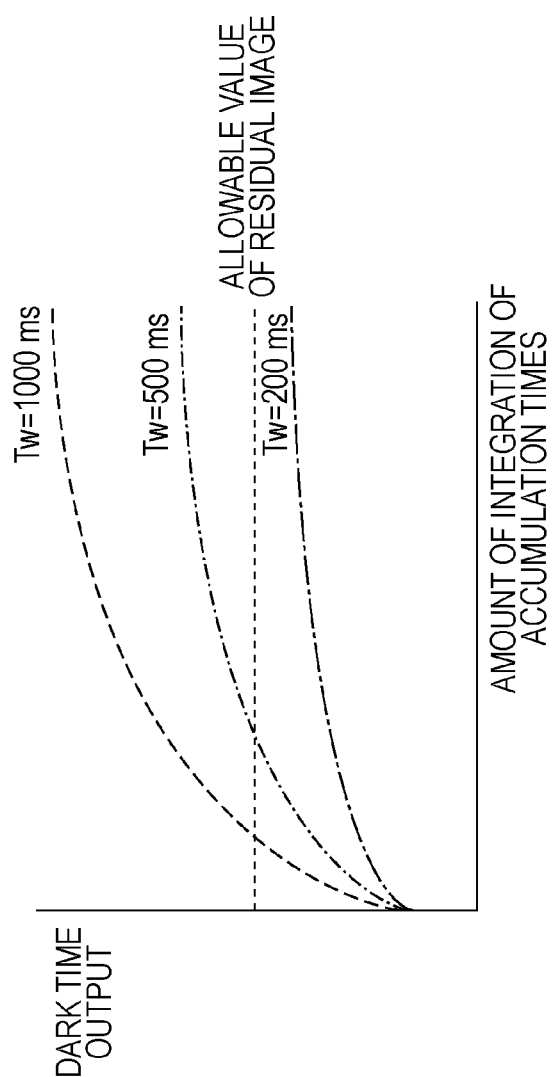
FIG. 5C is another characteristic diagram of the amount of integration of accumulation times and the dark time output illustrating the concept and advantages according to the embodiments of the present invention.

The arithmetic processing performed by the control computer will now be described with reference to FIGS. 5A to 5C. Referring to FIGS. 5B and 5C, the horizontal axis represents the amount of integration of the accumulation times in the FPD 104, and the vertical axis represents pixel output data acquired in the dark state as the dark time output.

How the difference in level on which the arithmetic processing according to the embodiments of the present invention is based occurs will now be described with reference to FIGS. 5B and 5C. As shown in FIG. 5B, the inventor found that the dark time output from the flat panel detector depends on the scanning history of the pixels, more specifically, depends on the amount of integration of the accumulation times since the bias voltage has been applied to the conversion element in the flat panel detector. The image capturing operation is performed in the first scanning area in the first image capturing operation in the first embodiment. Accordingly, the image capturing operation is performed multiple times to the pixels included in the first scanning area A, and the dark time output components accumulated during the accumulation operation are not completely output in each output operation and remains in the pixels. The components remaining in the pixels are used as the scanning history of the pixels. In contrast, the normal image capturing operation is not performed to the pixels included in the second scanning area B in the first image capturing operation. This is because, for example, the accumulation operation is constantly performed, the entire second scanning area B is scanned at one time, or the output operation of the pixels in the second scanning area B is performed in a scanning period shorter than that of the pixels in the first scanning area A. In such cases, the accumulation time in the first scanning area A is different from that in the second scanning area B. For example, when the output operation of the pixels in the second scanning area B is performed in a scanning period shorter than that of the pixels in the first scanning area A, the amount of integration of the accumulation times during the first image capturing operation for the pixels included in the first scanning area A becomes smaller than that for the pixels in the second scanning area B. As a result, the dark time output of the pixels included in the first scanning area A is denoted by A in FIG. 5B and the dark time output of the pixels included in the second scanning area B is denoted by B or C in FIG. 5B. The dark time output of the pixels included in the second scanning area B depends on the amount of integration of the accumulation times, which depends on the length of the period of the fluoroscopy operation and is denoted by B or C in FIG. 5B. Accordingly, a difference occurs between the dark time output A of the first scanning area and the dark time output C of the second scanning area and the difference in the dark time output is displayed as the difference in level. Particularly, the difference in the dark time output between the first scanning area and the second scanning area is increased with the increasing period of the fluoroscopy operation and, thus, the difference in level becomes more distinct. As described above, the dark time output of the flat panel detector depends on the amount of integration of the accumulation times, which is the scanning history of the pixels. Consequently, the inventor found that a difference in the dark time output occurs between the areas that are subjected to the scanning in the image capturing in the flat panel detector and the areas that are not subjected to the scanning in the image capturing in the flat panel detector to cause the difference in level, which is an image artifact caused by the scanning area.

As shown in FIG. 5C, the dark time output of the flat panel detector depends on the accumulation operation time Tw in the conversion element. Accordingly, the inventor found that the difference in level, which is an image artifact caused by the scanning area, depends on the amount of integration of the accumulation times before the scanning area is switched and the accumulation operation time Tw in the conversion element in the image capturing operation after the scanning area is switched. The inventor also found that, if the difference in level is smaller than a predetermined allowable value, the difference in level caused by the output difference in the image is not recognized and that the image captured by the imaging apparatus can be used. The predetermined allowable value is a value specific to the flat panel detector and can be acquired and set in advance, for example, in an inspection before shipment. Particularly, since the difference in level that is smaller than a random noise of the flat panel detector is generally buried in the random noise and is not recognized, the allowable value is preferably lower than the output level of the random noise.

As described above, the control computer 108 performs the arithmetic processing to determine the accumulation operation time in the image capturing operation after the scanning area is switched on the basis of the information about the amount of integration of the accumulation times in the image capturing operation before the scanning area is switched. The arithmetic processing is performed so that the image artifact caused by the scanning area is lower than the predetermined allowable value. As a result, the upper limit of the accumulation operation time is equal to the time when the difference in level is equal to the predetermined allowable value. However, it is necessary for the radiation generating apparatus 110 to generate the radiation in which the dosage necessary for the image capturing is ensured within a time width that is within the accumulation operation time. If the accumulation operation time is too short, a case can occur in which the dosage necessary for the image capturing cannot be ensured only in a short period that exceeds the limit of the radiation generating apparatus or only at a large intensity. In other words, the time when the radiation generating apparatus 110 can emit the radiation necessary for the image capturing corresponds to the lower limit of the accumulation operation time. Accordingly, the control computer 108 determines the accumulation operation time so that the difference in level becomes lower than the predetermined allowable value within a time range in which the radiation generating apparatus 110 can emit the radiation necessary for the image capturing after the scanning area is switched. However, if the arithmetic processing results in a short time that exceeds the limit of the radiation generating apparatus, the lower limit of the accumulation operation time is equal to a shortest radiation time, which is a limit time when the radiation generating apparatus can emit the radiation. In such a case, the control computer 108 controls the radiation generating apparatus so that the intensity of the emitted radiation is increased in order to ensure the dosage necessary for the image capturing. Specifically, the control computer 108 controls the tube current of the radiation source in the radiation generating apparatus to adjust the intensity of the radiation.

The control computer 108 supplies the control signal based on the determined accumulation operation time to the control unit in the imaging apparatus. The control unit controls the drive circuit so that the accumulation operation is performed in the FPD unit in the determined accumulation time. In addition, the control computer 108 supplies the control signal based on the determined accumulation operation time to the radiation control apparatus to control the radiation generating apparatus so that the radiation generating apparatus emits the radiation necessary for the image capturing after the scanning area is switched in accordance with the determined accumulation operation time.

An example of the configuration in which the arithmetic processing according to an embodiment of the present invention is performed and an example of the arithmetic processing will now be described with reference to FIG. 5A. Referring to FIG. 5A, the control computer 108 includes an image data processor 501, a sensor 502, an accumulation operation time determiner 503, and a characteristics storage part 504. The characteristics storage part 504 stores the amount of integration of the accumulation times in the first image capturing operation, the accumulation operation time in the second image capturing operation, and data concerning the dark time output, which indicates the characteristics of the FPD unit. A lookup table including such data is preferably used in the characteristics storage part 504. The characteristics storage part 504 also stores information concerning the shortest radiation time and a maximum output intensity in the radiation generating apparatus. In the embodiments of the present invention, the accumulation operation time determiner 503 and the characteristics storage part 504 are collectively referred to as an arithmetic processing unit 505.

The image data transmitted from the imaging apparatus 100 is subjected to the image processing in the image data processor 501 and is transmitted to the display apparatus 113. The control unit 106 in the imaging apparatus 100 transmits information about the scanning areas in the first image capturing operation, information about the frame speed in the first image capturing operation, and information about the time of the first image capturing operation to the sensor 502. The sensor 502 determines the accumulation times in units of frames for every scanning area on the basis of the received information and accumulates the determined accumulation times. Then, the sensor 502 adds the accumulated accumulation times in units of frames for every frame to acquire information about the amount of integration of the accumulation times in each scanning area in the image capturing operation and supplies the information to the accumulation operation time determiner 503. Instead of the information from the control unit 106, information transmitted from a photo timer (not shown) provided in the imaging apparatus separately from the FPD may be used. Alternatively, instead of the information from the control unit 106, information input in advance with the console 114 may be used. When the information from the console 114 is used, it is not necessary to add the accumulation times in units of frames and the information about the entire first image capturing operation may be acquired from the console 114. The sensor 502 may directly supply the information to the accumulation operation time determiner 503 without processing. In this case, the lookup table is preferably used in the characteristics storage part 504. The scanning area, the frame speed, and the scanning time in the first image capturing operation, the accumulation operation time in the second image capturing operation, and the data concerning the dark time output are stored in the lookup table.

Upon reception of an operator's input to instruct change of the radiation field, the console 114 transmits information concerning the dosage of the radiation necessary for the image capturing after the scanning area is switched to the accumulation operation time determiner 503. In response to the control signal from the console 114, the accumulation operation time determiner 503 determines the accumulation operation time Tw on the basis of the information about the amount of integration of the accumulation times in each scanning area, the information about the dosage of the radiation that is required, and the data stored in the characteristics storage part 504.

The determined accumulation operation time Tw is transmitted from the accumulation operation time determiner 503 to the control unit 106 in the imaging apparatus 100. The control unit 106 controls the drive circuit so that the accumulation operation is performed in the FPD unit in the input accumulation operation time Tw. The accumulation operation time Tw and the information about the dosage of the radiation that is required is transmitted from the accumulation operation time determiner 503 to the radiation control apparatus 109 to control the radiation generating apparatus 110 so that the radiation generating apparatus 110 emits the radiation necessary for the image capturing in accordance with the accumulation operation time Tw.

As described above, performing the image capturing operation after the scanning area is switched in accordance with the time based on the amount of integration of the accumulation times in the image capturing operation before the scanning area is switched allows the difference in level affected by the scanning area to be reduced without the complicated image processing, thus preventing a considerable reduction in image quality. Although the accumulation operation time Tw is determined in the first embodiment, the present invention is not limited to the determination of the accumulation operation time Tw. For example, both the accumulation operation time Tw and the time of the initialization operation K2 immediately before the accumulation operation time Tw may be calculated and determined and the control may be performed so that the image output operation X2 or the like is performed in combination with the initialization operation K2. Although the control computer 108 performs the arithmetic processing in the first embodiment, the present invention is not limited to this. The control unit 106 in the imaging apparatus 100 may perform the arithmetic processing in response to the control signal from the control computer 108. The second image capturing operation may be performed without the first image capturing operation and the switching of the scanning areas. In such a case, the arithmetic processing may be performed on the assumption that the amount of integration of the accumulation times in the first image capturing operation is equal to zero to determine the accumulation operation time in the second image capturing operation. The accumulation operation time in the second image capturing operation is increased in this case, compared with the case in which the first image capturing operation and the switching of the scanning areas are performed.

Second Embodiment

Figure 6A:
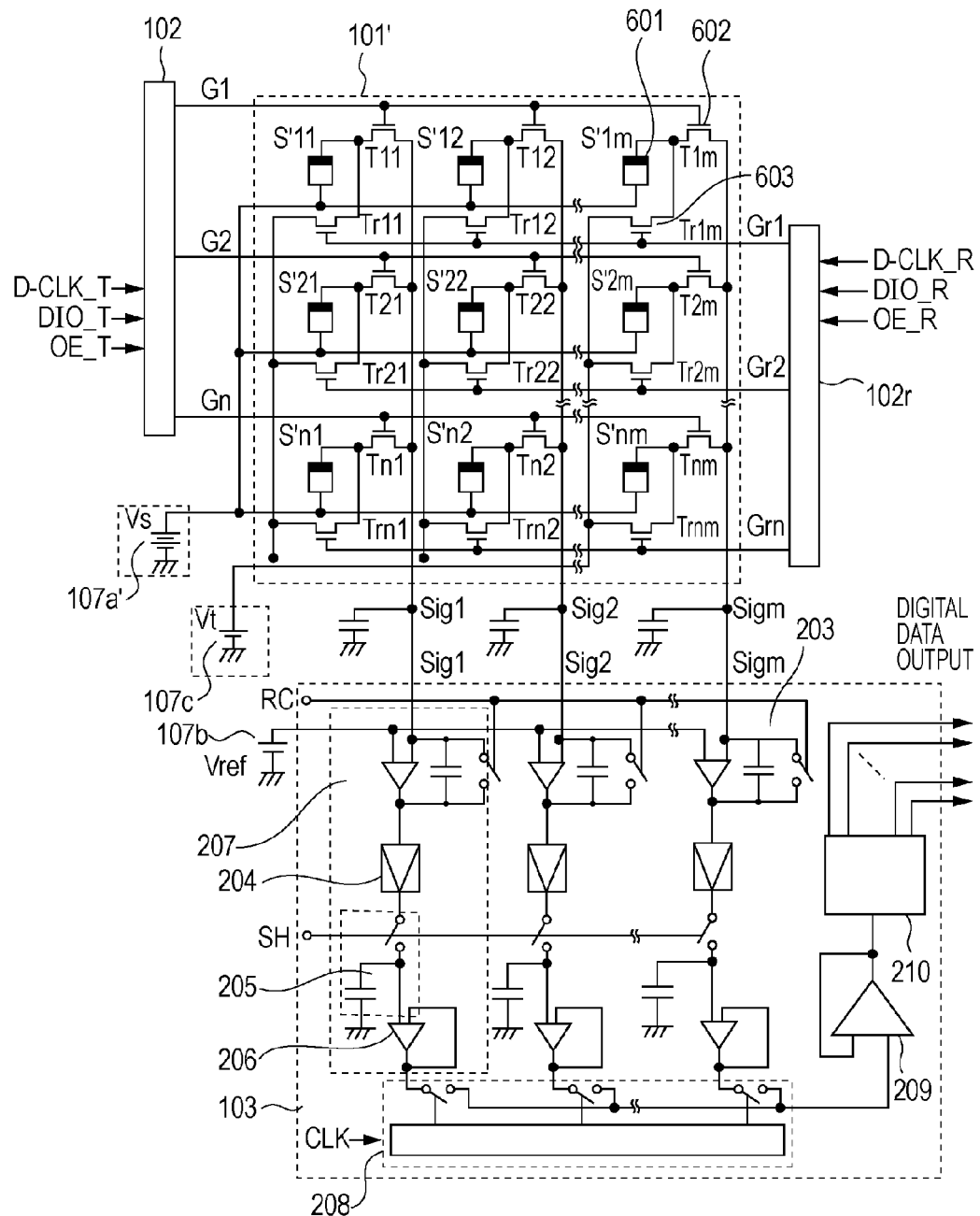
FIG. 6A is a conceptual equivalent circuit of an imaging apparatus according to a second embodiment of the present invention.

An imaging apparatus according to a second embodiment of the present invention will now be described with reference to FIGS. 6A and 6B. The same reference numerals are used in the second embodiment to identify the same components in the first embodiment. A detailed description of such components is omitted herein. Although the imaging apparatus including the FPD unit including pixels of n lines by m columns is shown in FIG. 6A for convenience, as in FIG. 2, the imaging apparatus practically includes the pixels of a number that is larger than n lines by m columns.

Although the PIN photodiode is used in the conversion element 201 in the detection unit 101 in the first embodiment, a photoelectric transducer having a metal insulator semiconductor (MIS) structure is used as a MIS-type conversion element in a conversion element 601 in a detection unit 101' in the second embodiment. Although one output switch element is provided for one pixel in the first embodiment, a refresh switch element 603 is provided, in addition to an output switch element 602, for one pixel in the second embodiment. One of the main terminals of the refresh switch element 603 is electrically connected to a first electrode 604 of the conversion element 601 and to one of the two main terminals of the output switch element 602. The other of the main terminals of the refresh switch element 603 is electrically connected to a refresh power supply 107c included in the power supply unit 107 via a common line. The control terminals of multiple refresh switch elements 603 in the line direction are commonly electrically connected to a refresh drive line Gr. Drive signals are applied from a refresh drive circuit 102r to the refresh switch elements 603 in each line via the refresh drive line Gr.

Figure 6B:
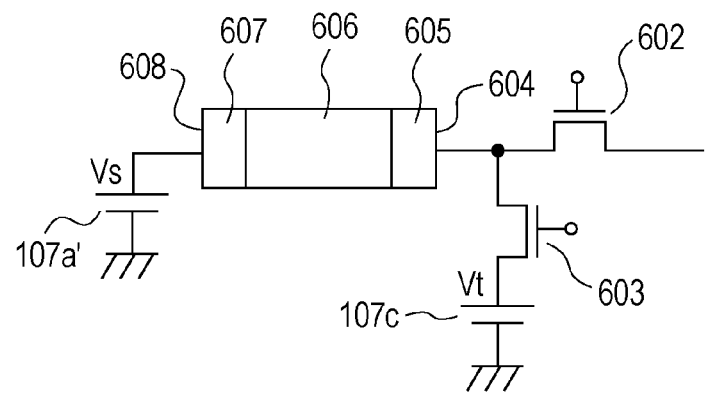
FIG. 6B is another conceptual equivalent circuit of the imaging apparatus according to the second embodiment of the present invention.

As shown in FIG. 6B, in the conversion element 601, a semiconductor layer 606 is provided between the first electrode 604 and a second electrode 608, an insulating layer 605 is provided between the first electrode 604 and the semiconductor layer 606, and an impurity semiconductor layer 607 is provided between the semiconductor layer 606 and the second electrode 608. The second electrode 608 is electrically connected to a bias power supply 107a' via the bias line Bs. The bias voltage Vs is supplied from the bias power supply 107a' to the second electrode 608 in the conversion element 601, and the reference voltage Vref is supplied to the first electrode 604 in the conversion element 601 via the output switch element 602 to perform the accumulation operation in the conversion element 601, as in the conversion element 201. In the fluoroscopy operation and the photography operation, a refresh voltage Vt is supplied to the first electrode 604 via the refresh switch element 603 and the conversion element 601 is refreshed with a bias |Vs-Vt|.

Figure 7A:
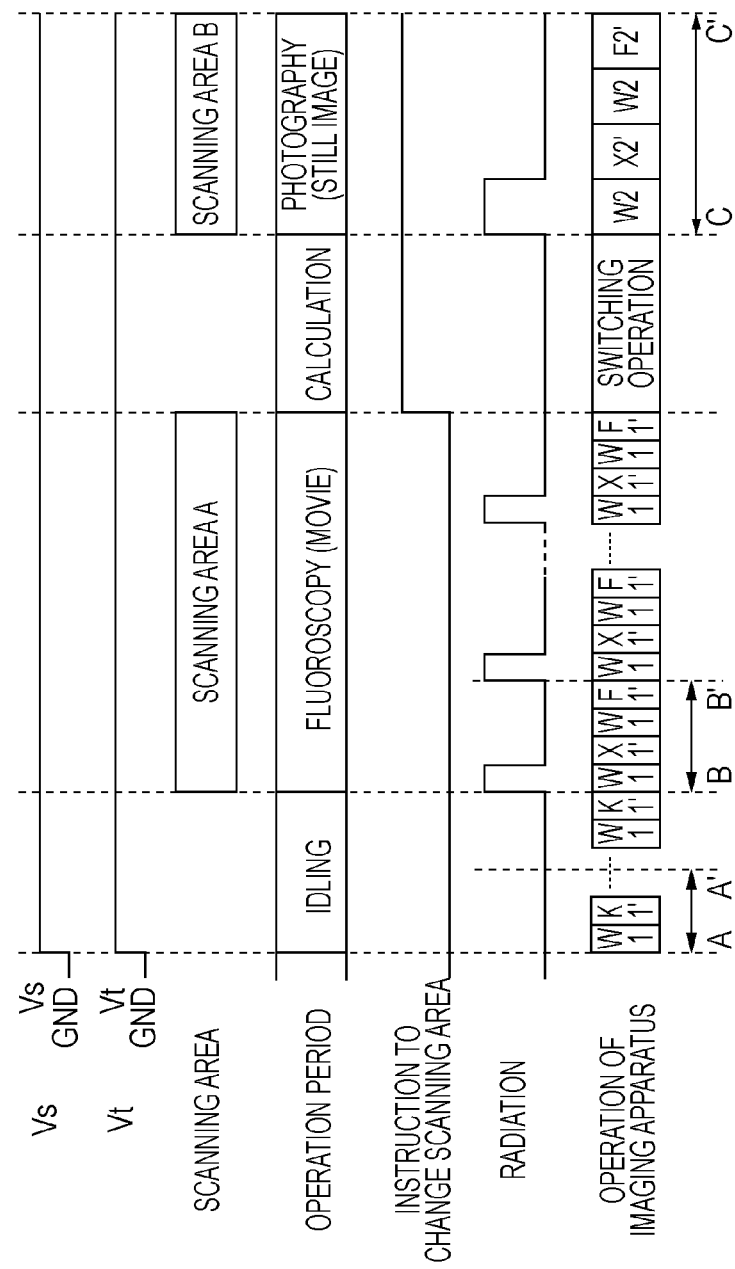
FIG. 7A is a timing chart illustrating the entire operation of the imaging apparatus and an imaging system according to the second embodiment of the present invention.

Examples of the operations of the imaging apparatus and the imaging system according to the second embodiment of the present invention will now be described with reference to FIGS. 7A to 7D. In the second embodiment, as shown in FIG. 7A, an initialization operation K1', an image output operation X1', and a dark image output operation F1' are performed, instead of the initialization operation K1, the image output operation X1, and the dark image output operation F1, respectively, in the first embodiment shown in FIG. 4A. In addition, an image output operation X2' and a dark image output operation F2' are performed, instead of the image output operation X2 and the dark image output operation F2, respectively, in the first embodiment shown in FIG. 4A. Furthermore, the imaging apparatus 100 performs a switching operation described in detail below during the arithmetic period in the second embodiment. The remaining operations are similar to the ones in the first embodiment. A detailed description of such operations is omitted herein. The operations that are different from those in the first embodiment will now be described with reference to FIGS. 7B to 7D.

Figure 7B:
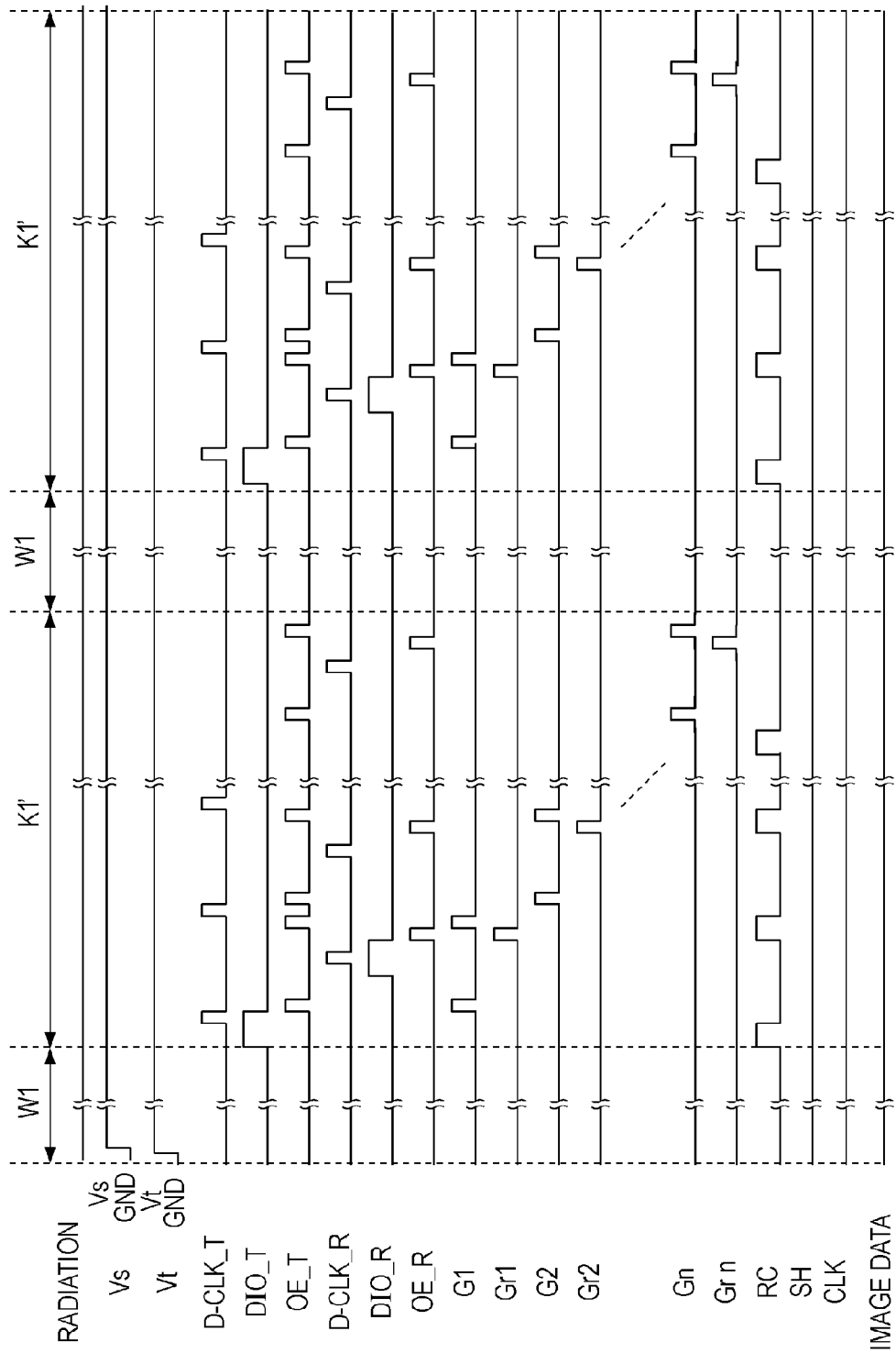
FIG. 7B is a timing chart illustrating an operation of the imaging apparatus and the imaging system according to the second embodiment of the present invention.

The detection unit 101' according to the second embodiment includes the refresh switch element 603, in addition to the output switch element 602, for one pixel. Accordingly, the initialization operation K1' in the idling operation in the second embodiment shown in FIG. 7B is different from the initialization operation K1 in which one conversion element 201 operates for one pixel. In the initialization operation K1', the conductive voltage Vcom is supplied from the drive circuit 102 to the drive line G to set the output switch element 602 to the conductive state and the electric charge in the conversion element 601 is output from the output switch element 602 as an electrical signal, as in the first embodiment. Then, the conductive voltage Vcom is supplied from the refresh drive circuit 102r to the refresh drive line Gr to set the refresh switch element 603 to the conductive state. At this time, the refresh voltage Vt is supplied from the refresh power supply 107c. As a result, the bias |Vs-Vt| is applied to the conversion element 601 to remove the electric charge remaining in the conversion element 601, thereby refreshing the conversion element 601. Then, the integration capacitor and the signal line are reset, the output switch element 602 is set to the conductive state again, and an initial bias |Vs-Vref| is applied to the conversion element 601 to initialize the conversion element 601. Sequentially performing the above operation in units of lines achieves the initialization operation K1'. As described above, since the remaining operations are similar to the ones in the first embodiment, a detailed description of such operations is omitted herein.

Figure 7C:
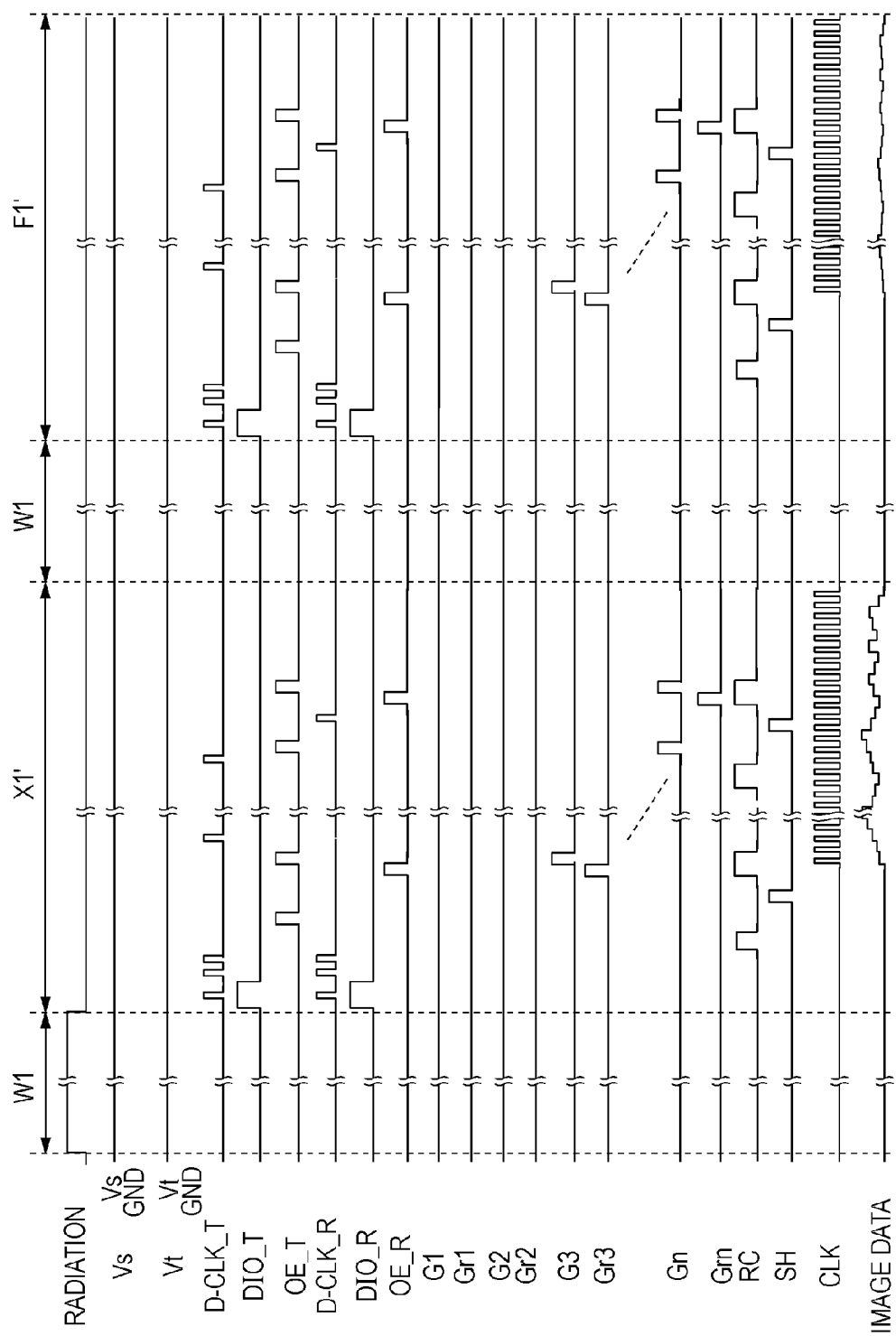
FIG. 7C is a timing chart illustrating another operation of the imaging apparatus and the imaging system according to the second embodiment of the present invention.

The difference between the image output operation X1' in the fluoroscopy operation in the second embodiment shown in FIG. 7C and the image output operation X1 and the difference between the dark image output operation F1' in the fluoroscopy operation in the second embodiment shown in FIG. 7C and the dark image output operation F1 are similar to the one between the initialization operation K1' and the initialization operation K1, described above. Since the remaining operations are similar to the ones in the first embodiment, a detailed description of such operations is omitted herein.

Figure 7D:
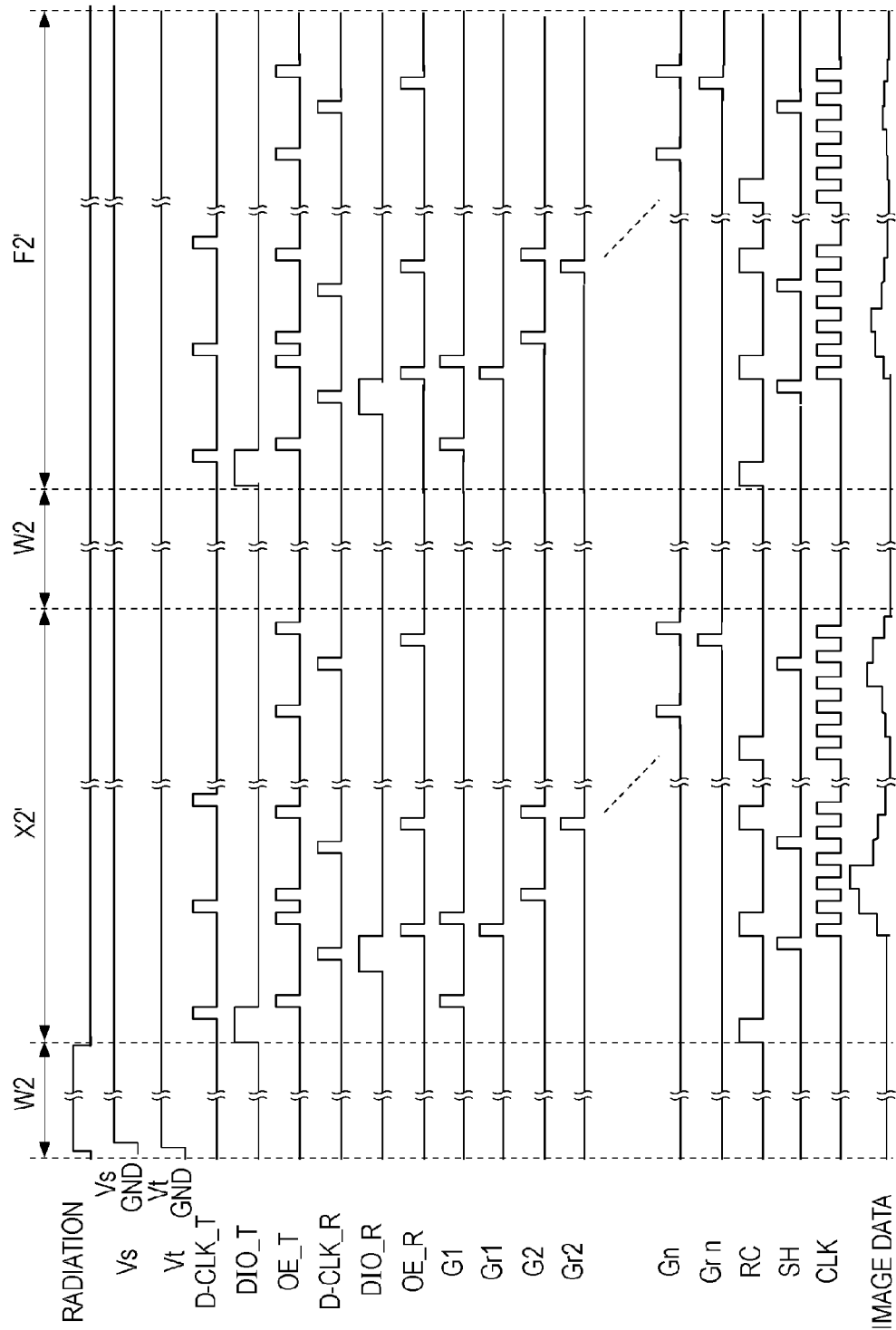
FIG. 7D is a timing chart illustrating another operation of the imaging apparatus and the imaging system according to the second embodiment of the present invention.

In the image output operation X2' and the dark image output operation F2' in the photography operation in the second embodiment shown in FIG. 7D, the conductive voltage Vcom is supplied from the drive circuit 102 to the drive line G to set the output switch element 602 to the conductive state, as in the first embodiment. As a result, the electric charge in the conversion element 601 is output from the output switch element 602 as an electrical signal in units of lines and image data is output from the imaging apparatus via the readout circuit 103. Then, the conductive voltage Vcom is supplied from the refresh drive circuit 102r to the refresh drive line Gr to set the refresh switch element 603 to the conductive state. At this time, the refresh voltage Vt is supplied from the refresh power supply 107c. As a result, the bias |Vs-Vt| is applied to the conversion element 601 to remove the electric charge remaining in the conversion element 601, thereby refreshing the conversion element 601. Then, the integration capacitor and the signal line are reset, the output switch element 602 is set to the conductive state again, and the initial bias |Vs-Vref| is applied to the conversion element 601 to initialize the conversion element 601. Sequentially performing the above operation in units of lines achieves the image output operation X2' or the dark image output operation F2'. Although the image output operation X2' is differentiated from the image output operation X1' because the period of the image output operation X2' is different from that of the image output operation X1', the image output operation X2' may be performed in the same period as that of the image output operation X1'.

The switching operation according to the second embodiment of the present invention will now be described with reference to FIGS. 8A to 8C.

Figure 8A:
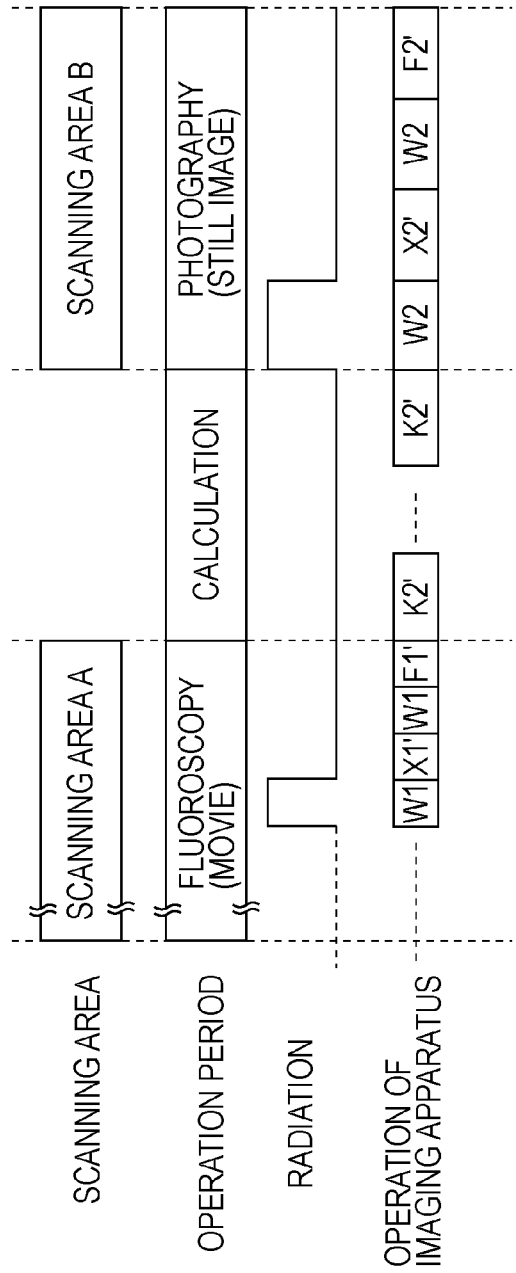
FIG. 8A is a timing chart illustrating an operation according to the second embodiment of the present invention.
Figure 8B:
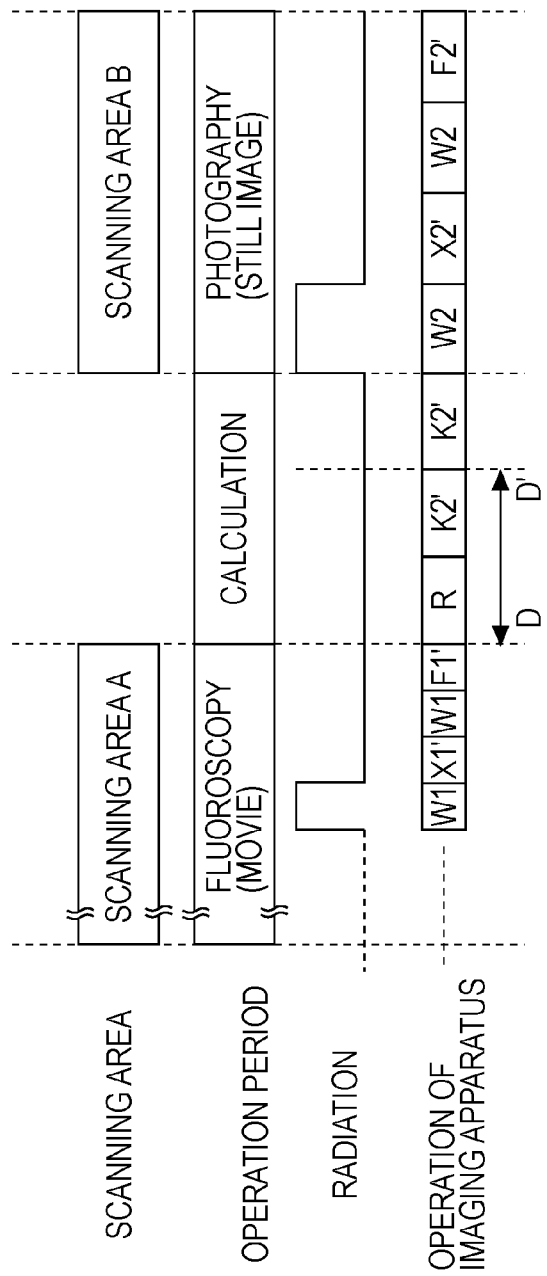
FIG. 8B is a timing chart illustrating another operation according to the second embodiment of the present invention.

In the switching operation shown in FIG. 8A, the FPD 104 performs the initialization operation K2' similar to the initialization operation K1 once or multiple times during the period having the same length as that of the period of the image output operation X2' and the dark image output operation F2' in the photography operation. In other words, the FPD 104 performs the initialization operation K2' corresponding to the image output operation X2' or the dark image output operation F2' in the photography operation performed after the scanning area is switched once or multiple times. In the initialization operation K2', the switching operation is performed by the initialization operation corresponding to the image capturing operation performed after change and superior image data having a little amount of image artifact can be acquired. Since the accumulation operation is not performed, it is possible to rapidly stabilize the characteristics of the conversion element. Particularly, as the switching operation including the multiple initialization operations, the initialization operation corresponding to the image capturing operation performed after change is preferably performed at least once immediately before the image capturing operation performed after change.

In the switching operation shown in FIG. 8B, the FPD 104 performs a refresh operation R described below at least once.

Then, the FPD 104 performs the initialization operation K2' corresponding to the image output operation X2' or the dark image output operation F2' in the photography operation performed after the change of the radiation field that is performed after the scanning area is switched once or multiple times. With this switching operation, in addition to the advantages of the switching operation shown in FIG. 8A, it is possible to further reduce the difference in level because the electric charge remaining in the conversion element is removed in the refresh operation R. The refresh operation will now be described with reference to FIG. 8C.

Figure 8C:
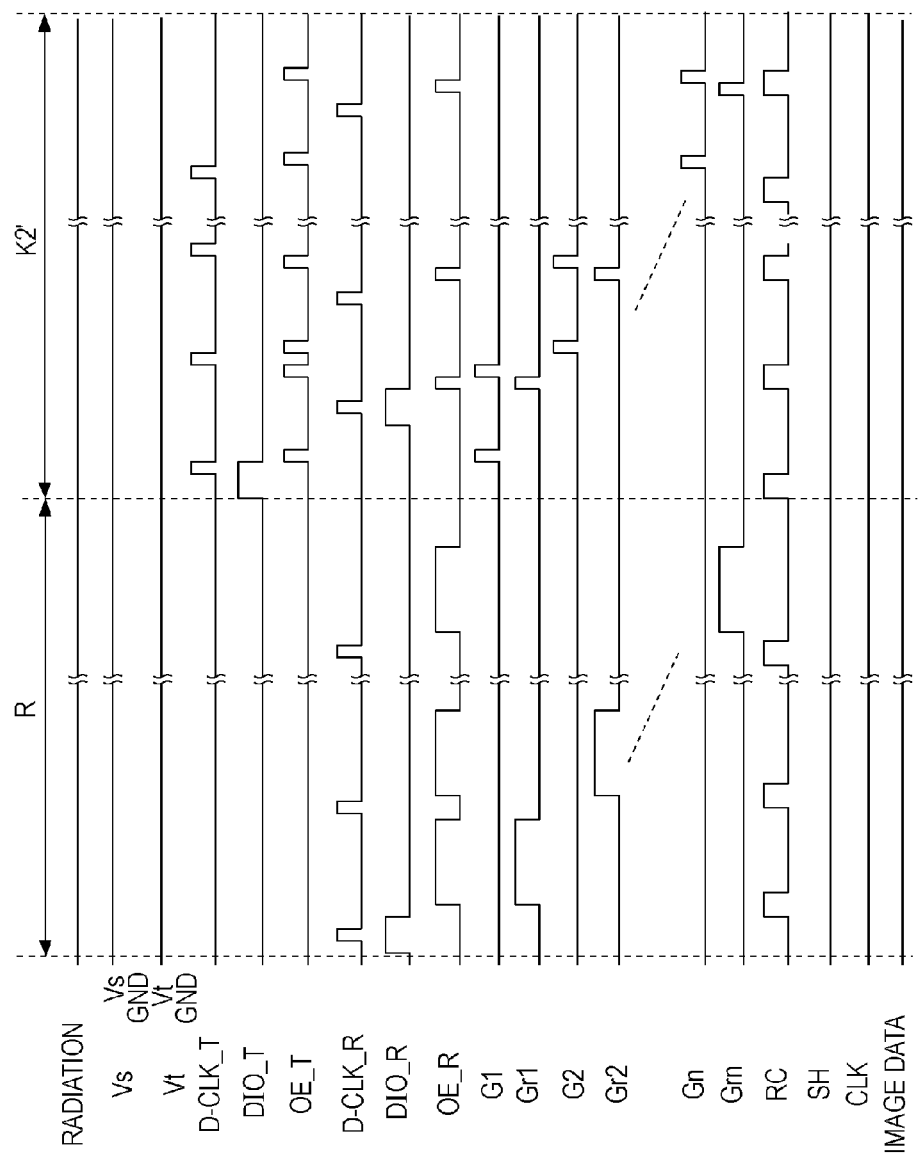
FIG. 8C is a timing chart illustrating another operation according to the second embodiment of the present invention.

In the refresh operation shown in FIG. 8C, the drive circuit 102 does not apply the conductive voltage Vcom to the output switch element 602 and the output switch element 602 is kept in the non-conductive state. In this state, the refresh drive circuit 102r applies the conductive voltage Vcom to the refresh switch element 603 in units of lines to set the refresh switch element 603 to the conductive state. As a result, the bias |Vs-Vt| is applied to the conversion element 601 to remove the electric charge remaining in the conversion element 601, thereby refreshing the conversion element 601. Sequentially performing the above operation in units of lines achieves the refresh operation R.

After the refresh operation R, the integration capacitor and the signal line are reset, the conductive voltage Vcom is applied from the drive circuit 102 to the drive line G to set the output switch element 602 to the conductive state, and the electric charge in the conversion element 601 is output from the output switch element 602 as an electrical signal. Then, the conductive voltage Vcom is applied from the refresh drive circuit 102r to the refresh drive line Gr to set the refresh switch element 603 to the conductive state. At this time, the refresh voltage Vt is applied from the refresh power supply 107c. As a result, the bias |Vs-Vt| is applied to the conversion element 601 to remove the electric charge remaining in the conversion element 601, thereby refreshing the conversion element 601 again. Then, the integration capacitor and the signal line are reset, the output switch element 602 is set to the conductive state again, and the initial bias |Vs-Vref| is applied to the conversion element 601 to initialize the conversion element 601. Sequentially performing the above operation in units of lines achieves the initialization operation K2'.

Also in the second embodiment, the second image capturing operation may include the initialization operation, as in the first embodiment.

The imaging apparatus 100 performs the switching operation during the arithmetic period, in addition to performing the image capturing operation after the radiation field is switched in the accumulation time based on the integral dose of the radiation in the image capturing operation before the radiation field is switched, in the second embodiment. Accordingly, in addition to the advantages of the first embodiment, it is possible to decrease the amount of the difference in level included in the image data output from the imaging apparatus 100 to further reduce the difference in level.

The embodiments of the present invention may be realized by, for example, a program executed by a computer included in the control unit 106. A unit to supply the program to the computer, for example, a computer-readable recording medium, such as a compact disc-read only memory (CD-ROM), having the program recorded therein or a communication medium, such as the Internet, over which the program is transmitted is also applicable as an embodiment of the present invention. In addition, the program is also applicable as an embodiment of the present invention. The program, the recording medium, the communication medium, and the program product are within the scope of the present invention. A combination easily supposed from the first or second embodiment is also within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-204719, filed Sep. 4, 2009, and Japanese Patent Application No. 2010-159885, filed Jul. 14, 2010, which are hereby incorporated by reference herein in their entirety.

REFERENCE SIGNS LIST 100 imaging apparatus
101 detection unit
102 drive circuit
103 readout circuit
104 flat panel detector
105 signal processing unit
106 control unit
107 power supply unit
108 control computer
109 radiation control apparatus
110 radiation generating apparatus
111 radiation source
112 radiation field limiting mechanism
113 display apparatus

The invention claimed is:

1. An imaging system comprising:
an imaging apparatus including a detector in which a plurality of pixels each including a conversion element that converts radiation or light into an electric charge are arranged in a matrix form and which performs an image capturing operation to output image data corresponding to radiation or light that is emitted, and a control unit that controls operations including the image capturing operation of the detector; and
a control computer configured to control the imaging apparatus,
wherein the image capturing operation includes a first image capturing operation and a second image capturing operation, the first image capturing operation including a first accumulation operation in which the conversion element generates the electric charge and a first output operation in which the detector is scanned in a first scanning area corresponding to part of the plurality of pixels to output image data in the first scanning area, the second image capturing operation including a second accumulation operation in which the conversion element generates the electric charge and a second output operation in which the detector is scanned in a second scanning area larger than the first scanning area to output image data in the second scanning area,
wherein, if switching from the first scanning area to the second scanning area is performed, the control computer performs arithmetic processing so that an image artifact caused by the scanning area is lower than a predetermined allowable value on the basis of information about the amount of integration of accumulation times in the first image capturing operation and supplies a control signal based on the time of the second accumulation operation determined in the arithmetic processing to the control unit, and
wherein the control unit controls the operation of the detector so that the second accumulation operation is performed in the time of the second accumulation operation determined in the arithmetic processing.

2. The imaging system according to claim 1,
wherein the control computer includes a characteristics storage part, a sensor, and an accumulation operation time determiner,
wherein the characteristics storage part stores the amount of integration of accumulation times in the first image capturing operation, the time of the accumulation operation, data concerning a dark time output, and information about a shortest radiation time and a maximum output intensity in a radiation generating apparatus, which indicate characteristics of the detector,
wherein the sensor supplies information about the amount of integration of accumulation times to the accumulation operation time determiner, and
wherein the accumulation operation time determiner determines the time of the accumulation time in the second image capturing operation on the basis of the information about the amount of integration of accumulation times and the data and the information stored in the characteristics storage part.

3. The imaging system according to claim 2, further comprising:
a console configured to supply information about the dosage of the radiation necessary for the second image capturing operation to the control computer,
wherein the accumulation operation time determiner determines the time of the accumulation operation on the basis of the information about the dosage of the radiation necessary for the second image capturing operation.

4. The imaging system according to claim 2,
wherein the arithmetic processing determines the time of the accumulation operation using the shortest radiation time in the radiation generating apparatus as a lower limit.

5. The imaging system according to claim 1,
wherein each of the pixels further includes a switch element that outputs an electrical signal corresponding to the electric charge,
wherein the detector includes a detection unit in which the pixels are arranged in a matrix form, a drive circuit that controls a conductive state of the switch element to drive the detection unit, and a readout circuit that outputs the electrical signal supplied from the detection unit through a signal line connected to the switch element as image data,
wherein the readout circuit includes a reset switch that resets the signal line, and
wherein the control unit controls the drive circuit and the reset switch so that the detector performs an initialization operation to initialize the conversion element during a period between the first image capturing operation and the second image capturing operation, in conjunction with the switching from the first scanning area to the second scanning area.

6. The imaging system according to claim 5, further comprising:
a power supply unit including a reference power supply that applies a reference voltage to one electrode of the conversion element through the switch element, a refresh power supply that applies a refresh voltage to the one electrode of the conversion element through the switch element, and a bias power supply that applies a bias voltage to the other electrode of the conversion element, wherein the conversion element is a metal insulator semiconductor (MIS)-type conversion element, wherein the detector performs a refresh operation in which the switch element is set to a non-conductive state, another switch element is set to the conductive state, the bias voltage is applied to the other electrode, and the refresh voltage is applied to the other electrode through the other switch element to refresh the conversion element, and wherein the control unit causes the detector to perform the refresh operation and the initialization operation after the refresh operation during the period.

7. An imaging apparatus comprising:
a detector in which a plurality of pixels each including a conversion element that converts radiation or light into an electric charge are arranged in a matrix form and which performs an image capturing operation to output image data corresponding to radiation or light that is emitted; and
a control unit configured to control operations including the image capturing operation of the detector,
wherein the image capturing operation includes a first image capturing operation and a second image capturing operation, the first image capturing operation including a first accumulation operation in which the conversion element generates the electric charge and a first output operation in which the detector is scanned in a first scanning area corresponding to part of the plurality of pixels to output image data in the first scanning area, the second image capturing operation including a second accumulation operation in which the conversion element generates the electric charge and a second output operation in which the detector is scanned in a second scanning area larger than the first scanning area to output image data in the second scanning area, and
wherein, if switching from the first scanning area to the second scanning area is performed, the control unit causes the detector to perform the second accumulation operation in a time determined by arithmetic processing so that an image artifact caused by the scanning area is lower than a predetermined allowable value on the basis of information about the amount of integration of accumulation times in the first image capturing operation.

8. A method of controlling an imaging apparatus that includes a detector in which a plurality of pixels each including a conversion element that converts radiation or light into an electric charge are arranged in a matrix form and which performs an image capturing operation to output image data corresponding to radiation or light that is emitted and that controls operations including the image capturing operation of the detector, the method comprising the step of:
performing a second image capturing operation after a first image capturing operation, the first image capturing operation including a first accumulation operation in which the conversion element generates the electric charge and a first output operation in which the detector is scanned in a first scanning area corresponding to part of the plurality of pixels to output image data in the first scanning area, the second image capturing operation including a second accumulation operation in which the conversion element generates the electric charge and which is performed in a time determined in arithmetic processing so that an image artifact caused by the scanning area is lower than a predetermined allowable value on the basis of information about the amount of integration of accumulation times in the first image capturing operation and a second output operation in which the detector is scanned in a second scanning area larger than the first scanning area to output image data in the second scanning area.

* * * * *